US011883137B2

(12) United States Patent
Nakagawa et al.

(10) Patent No.: US 11,883,137 B2
(45) Date of Patent: Jan. 30, 2024

(54) SENSOR MODULE, METHOD FOR MANUFACTURING SENSOR MODULE, AND BLOOD PRESSURE MEASUREMENT DEVICE

(71) Applicant: OMRON HEALTHCARE Co., Ltd., Kyoto (JP)

(72) Inventors: Yuki Nakagawa, Kyoto (JP); Iwanori Namba, Kyoto (JP); Katsunori Kondo, Kyoto (JP); Tsuyoshi Hamaguchi, Kyoto (JP); Takashi Fuchimoto, Kyoto (JP); Takuya Katagiri, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 701 days.

(21) Appl. No.: 16/950,467

(22) Filed: Nov. 17, 2020

(65) Prior Publication Data

US 2021/0068679 A1     Mar. 11, 2021

Related U.S. Application Data

(63) Continuation of application No. PCT/JP2019/020049, filed on May 21, 2019.

(30) Foreign Application Priority Data

May 24, 2018  (JP) ................. 2018-099715

(51) Int. Cl.
*A61B 5/021*  (2006.01)
*A61B 5/00*   (2006.01)

(52) U.S. Cl.
CPC .......... *A61B 5/02141* (2013.01); *A61B 5/681* (2013.01); *A61B 5/6824* (2013.01); *A61B 5/6843* (2013.01); *A61B 2562/043* (2013.01)

(58) Field of Classification Search
CPC ... A61B 5/02141; A61B 5/681; A61B 5/6824; A61B 5/6843; A61B 2562/043; A61B 5/021; A61B 5/022

See application file for complete search history.

(56) References Cited

U.S. PATENT DOCUMENTS

| 2004/0010198 A1* | 1/2004 | Yamakoshi | ........ A61B 5/02233 600/499 |
|---|---|---|---|
| 2006/0184054 A1* | 8/2006 | Sano | ...................... A61B 5/021 600/499 |

(Continued)

FOREIGN PATENT DOCUMENTS

| JP | H01288228 A | 11/1989 |
|---|---|---|
| JP | 2010-233883 A | 10/2010 |

(Continued)

OTHER PUBLICATIONS

International Preliminary Report on Patentability dated Nov. 26, 2020 in International (PCT) Application No. PCT/JP2019/020049.

*Primary Examiner* — Eric F Winakur
(74) *Attorney, Agent, or Firm* — Wenderoth, Lind & Ponack, L.L.P.

(57) ABSTRACT

Provided is a sensor module, a method for manufacturing a sensor module, and a blood pressure measurement device with a highly smooth surface and high sensor accuracy. A sensor module 63 includes: a pressure sensor portion 71; a sensor base 72 including a support wall portion 72a with flow holes 72d to 72g formed extending through the support wall portion 72a from one main surface side to the other main surface side, the pressure sensor portion 71 being disposed on the one main surface side of the sensor base 72; a sensor head cover 73 including an opening 73a at a position opposite a sensor 71a and disposed on the one main surface side of the support wall portion 72a of the sensor base 72 with a gap 79 that communicates with the flow holes (Continued)

72*d* to 72*g* and the opening 73*a* formed therebetween; and a soft portion 74 disposed in the opening 73*a* that covers the pressure sensor portion 71.

20 Claims, 29 Drawing Sheets

(56) References Cited

U.S. PATENT DOCUMENTS

2017/0347893 A1* 12/2017 Osoegawa ......... A61B 5/02233
2019/0167127 A1*  6/2019 Yoshino ............ A61B 5/02233

FOREIGN PATENT DOCUMENTS

| | | |
|---|---|---|
| JP | 2011-200267 A | 10/2011 |
| JP | 2015-144628 A | 8/2015 |
| JP | 2016-72589 A | 5/2016 |

* cited by examiner

[FIG. 1]
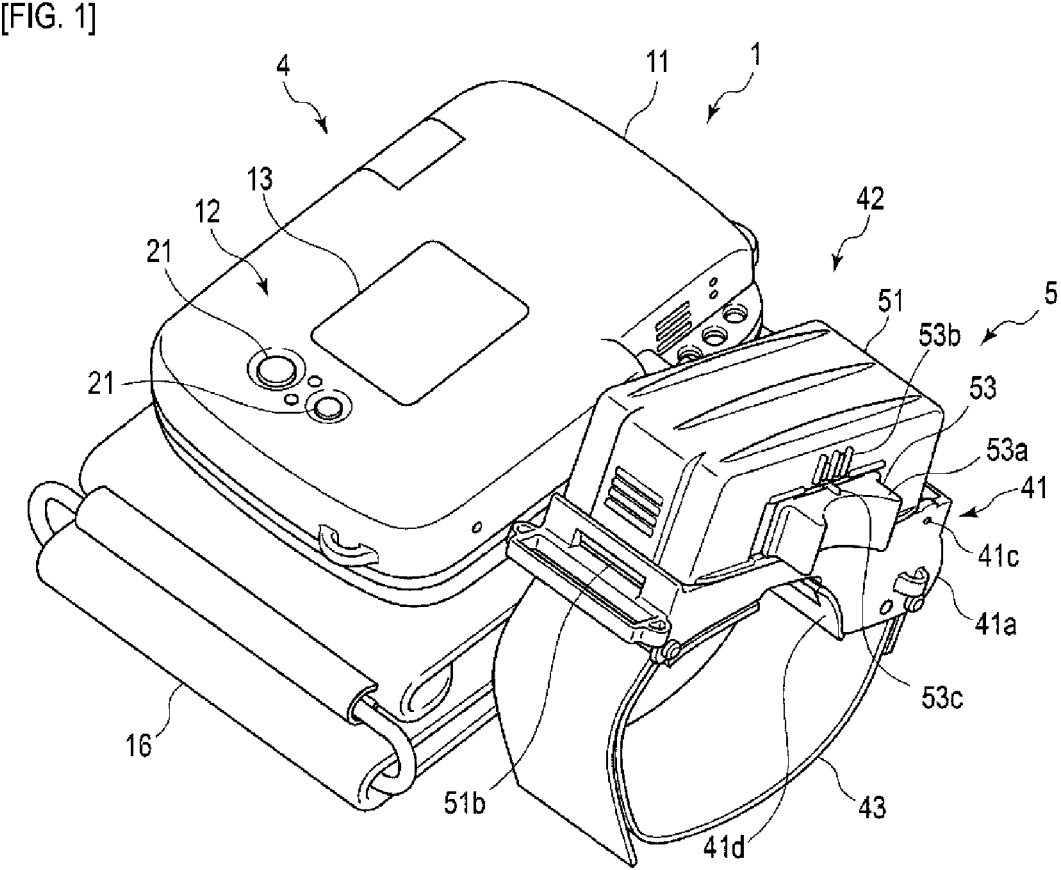

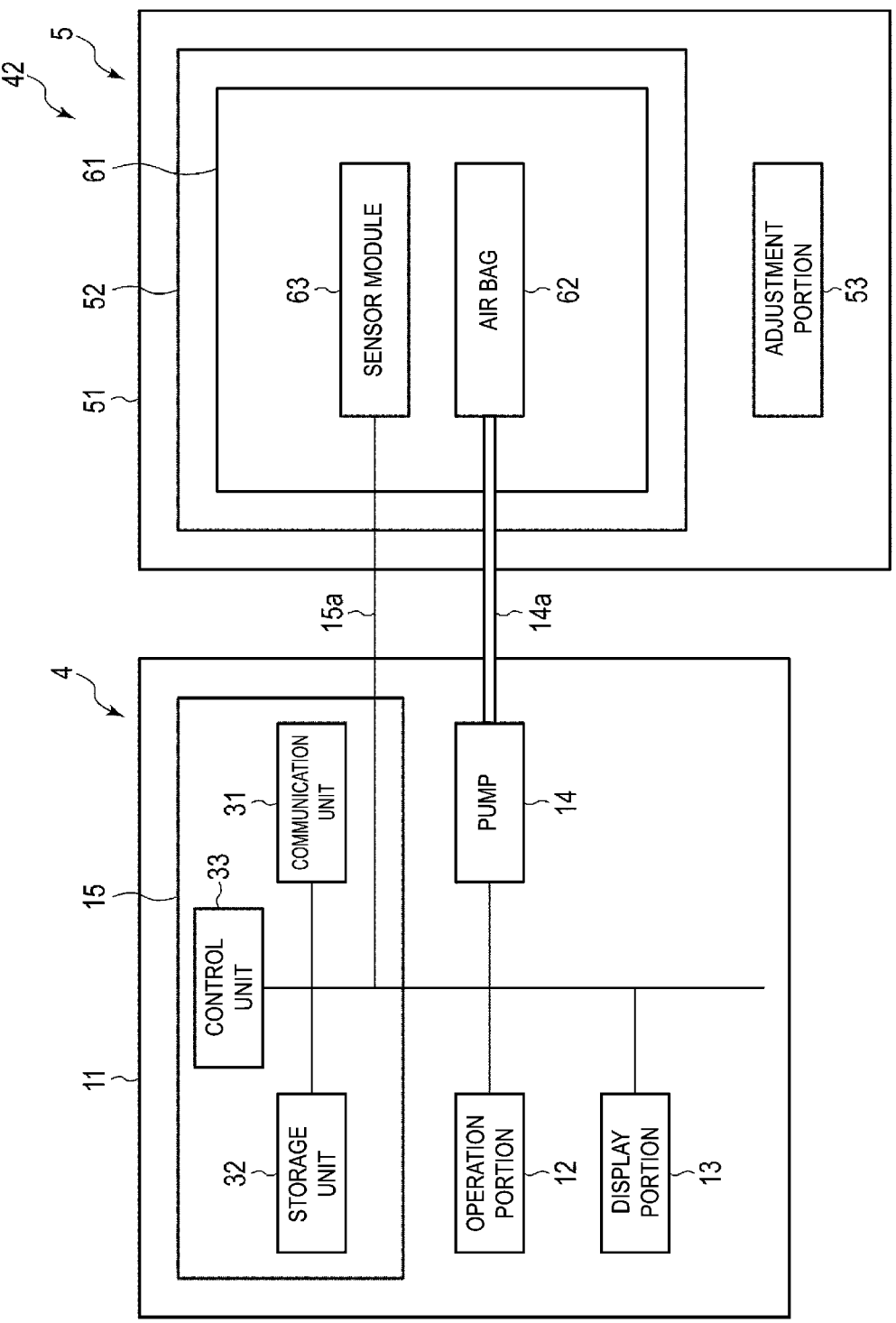
[FIG. 2]

[FIG. 3]
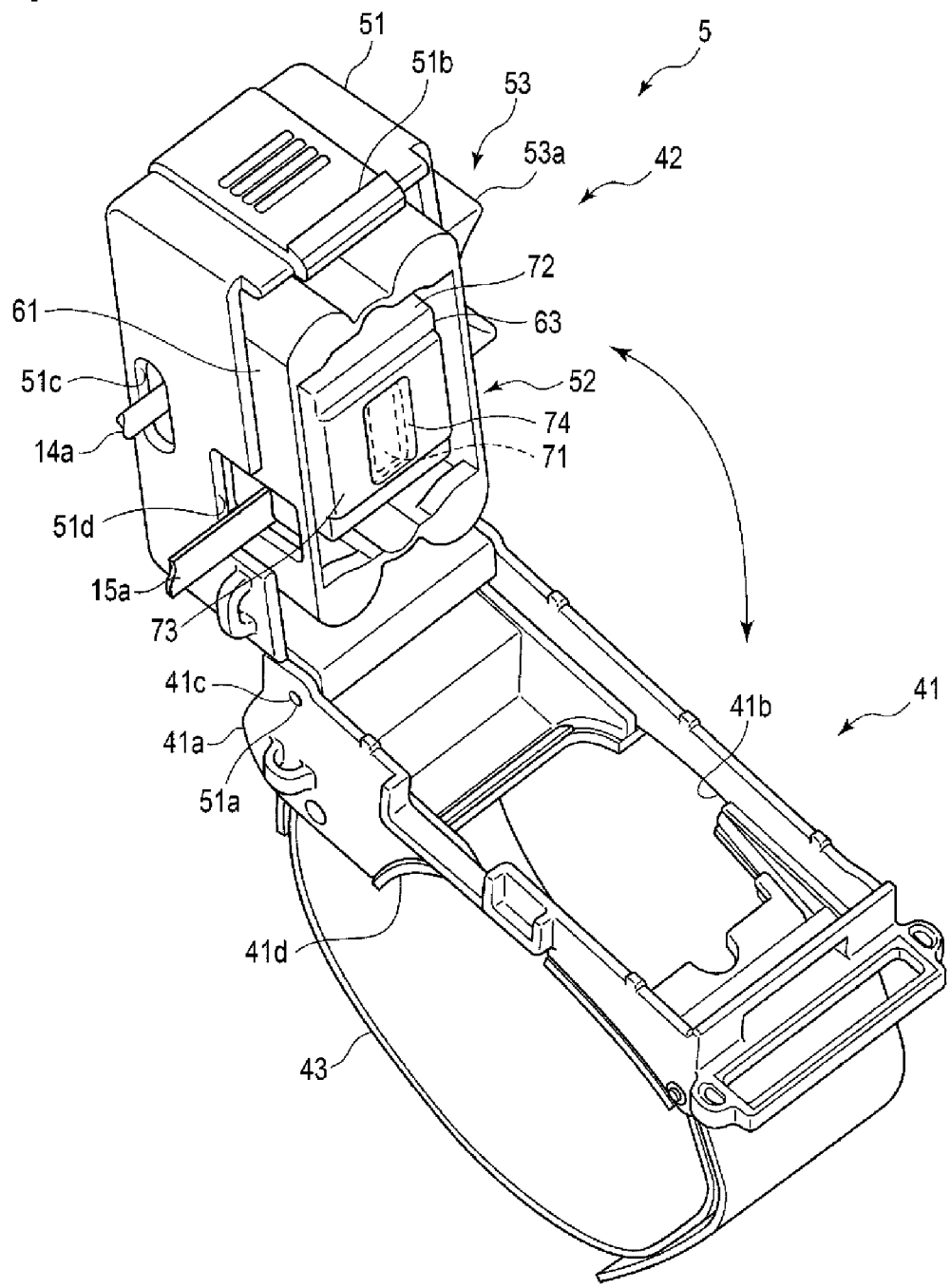

[FIG. 4]
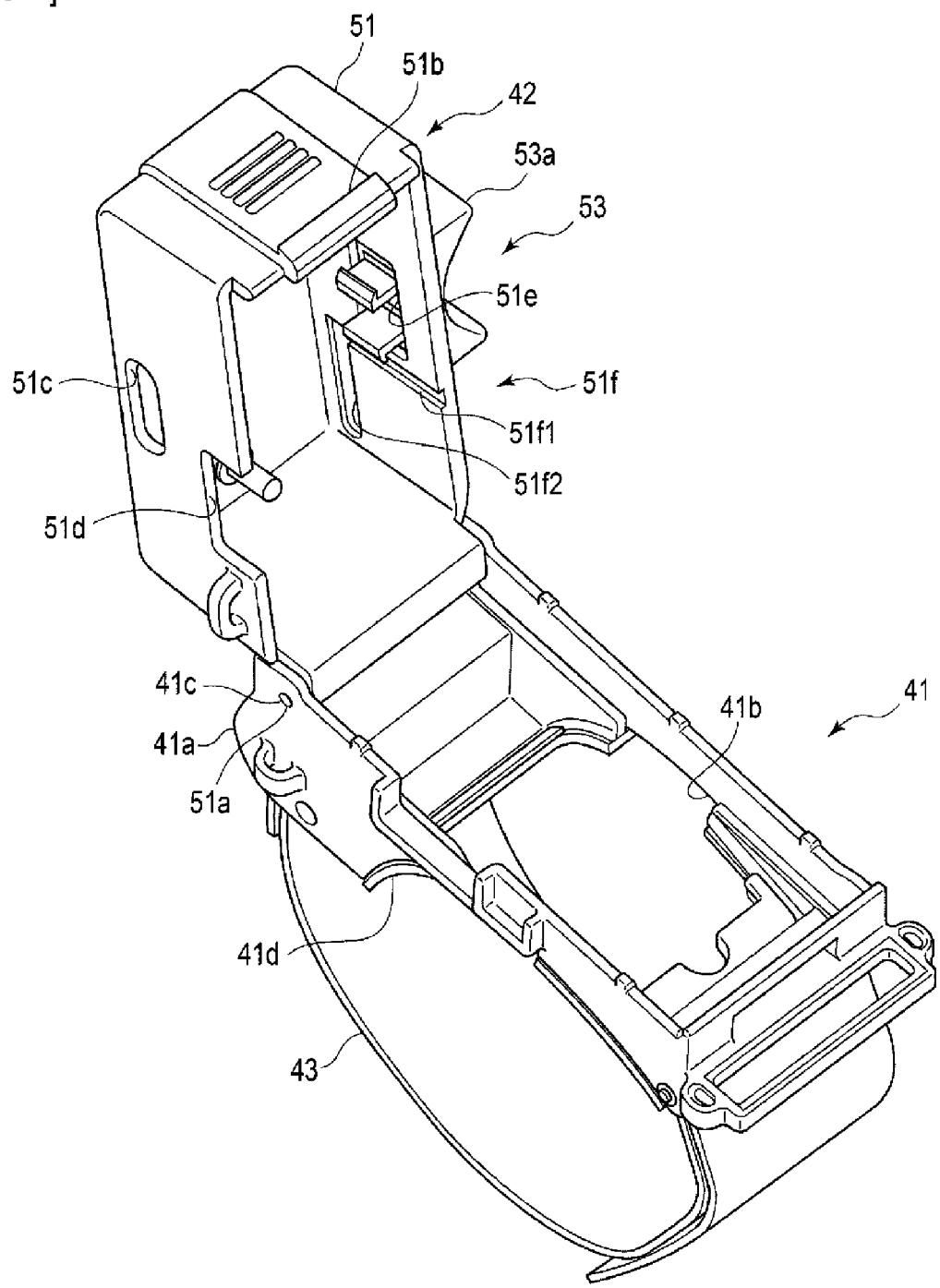

[FIG. 5]
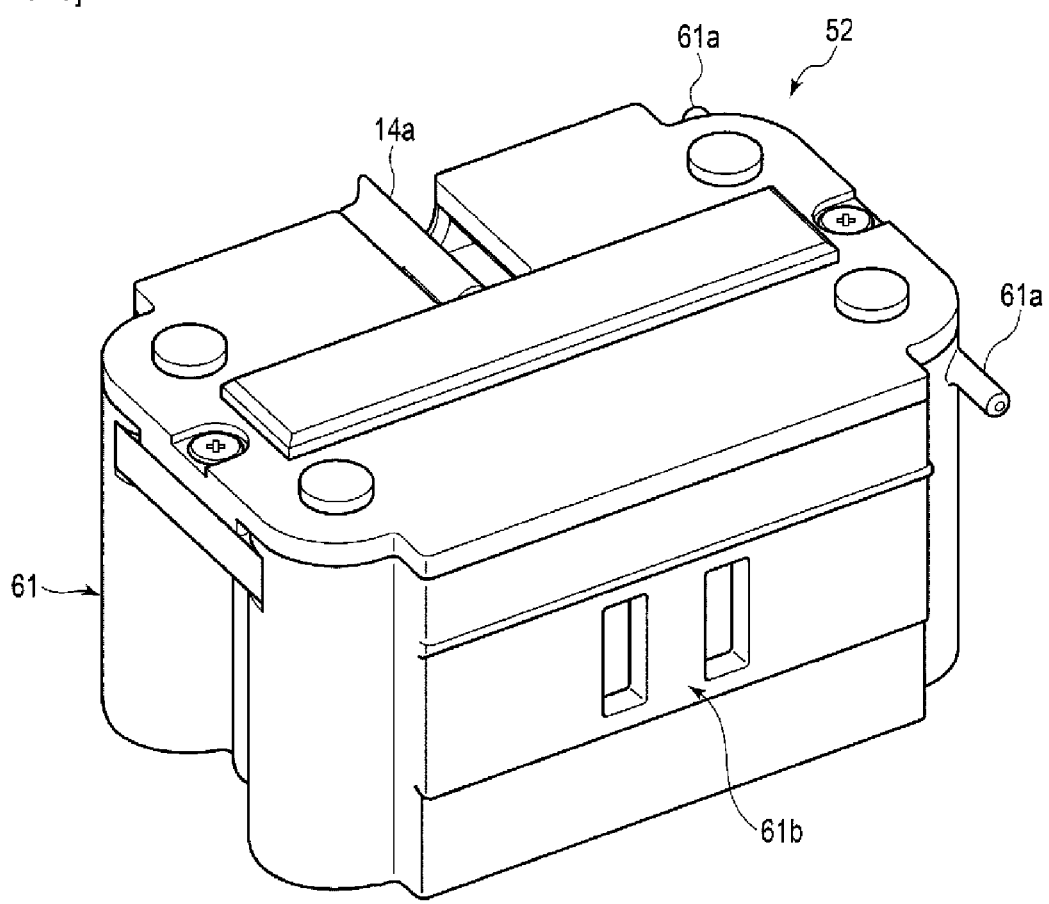

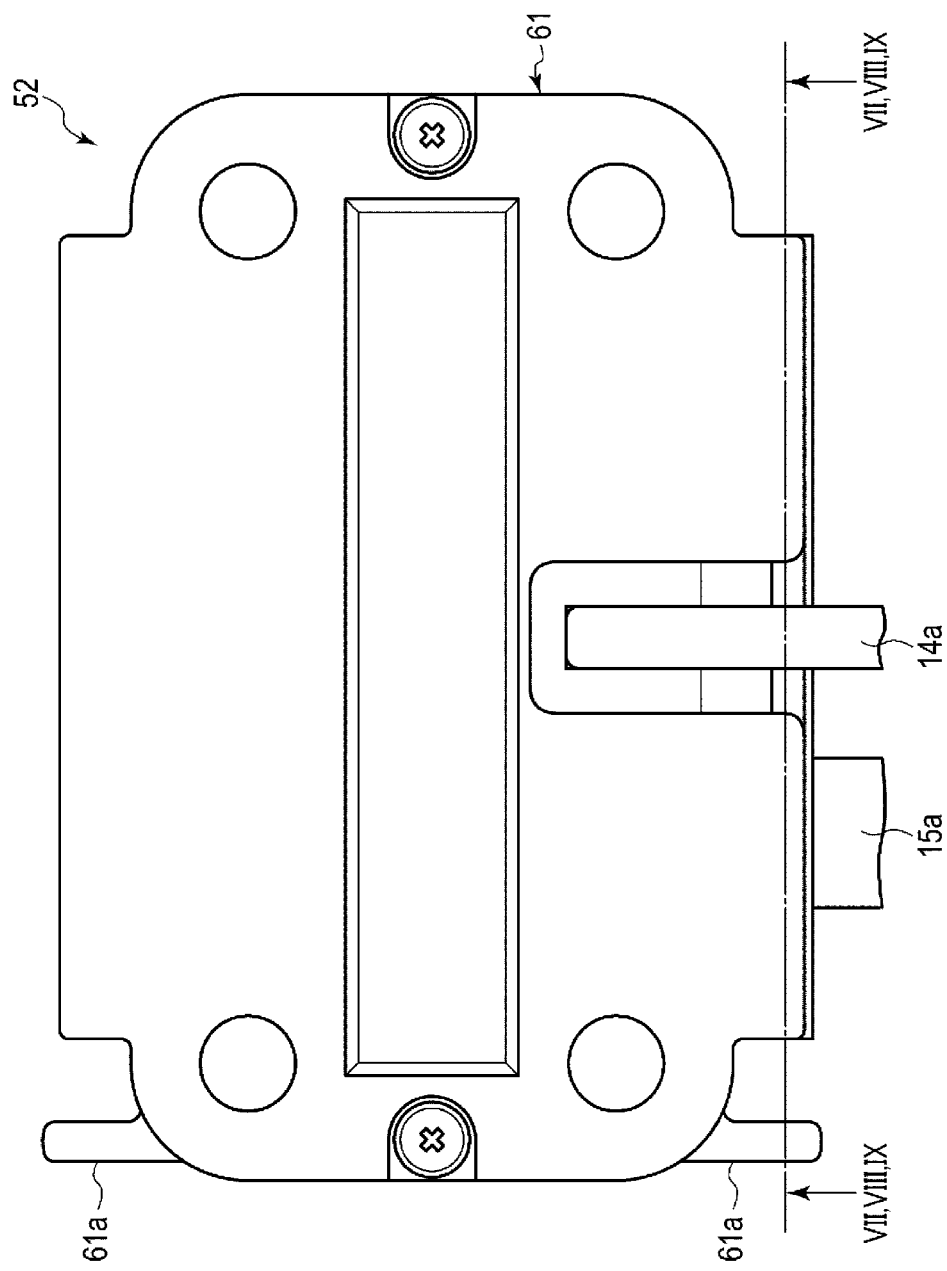

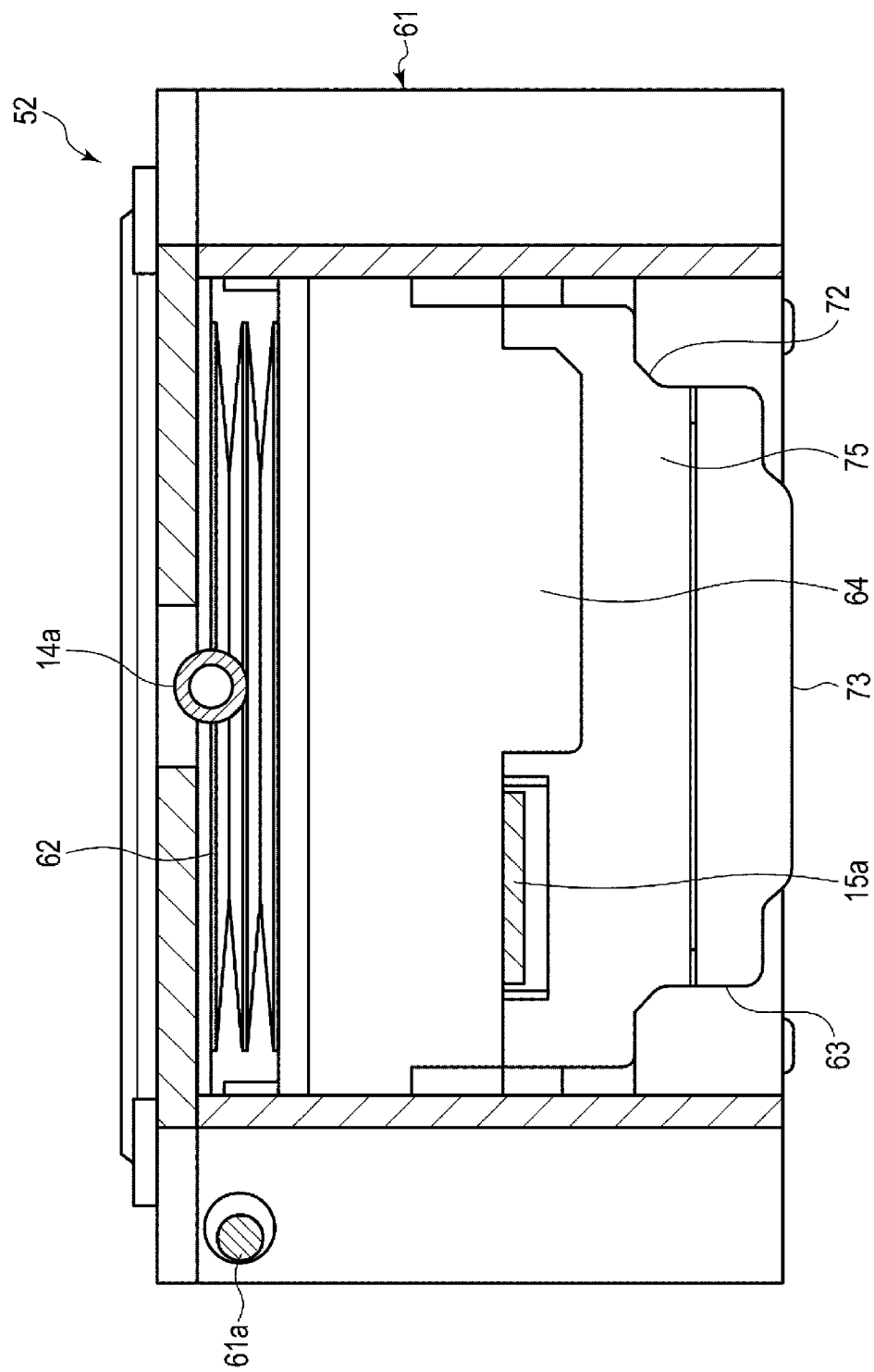

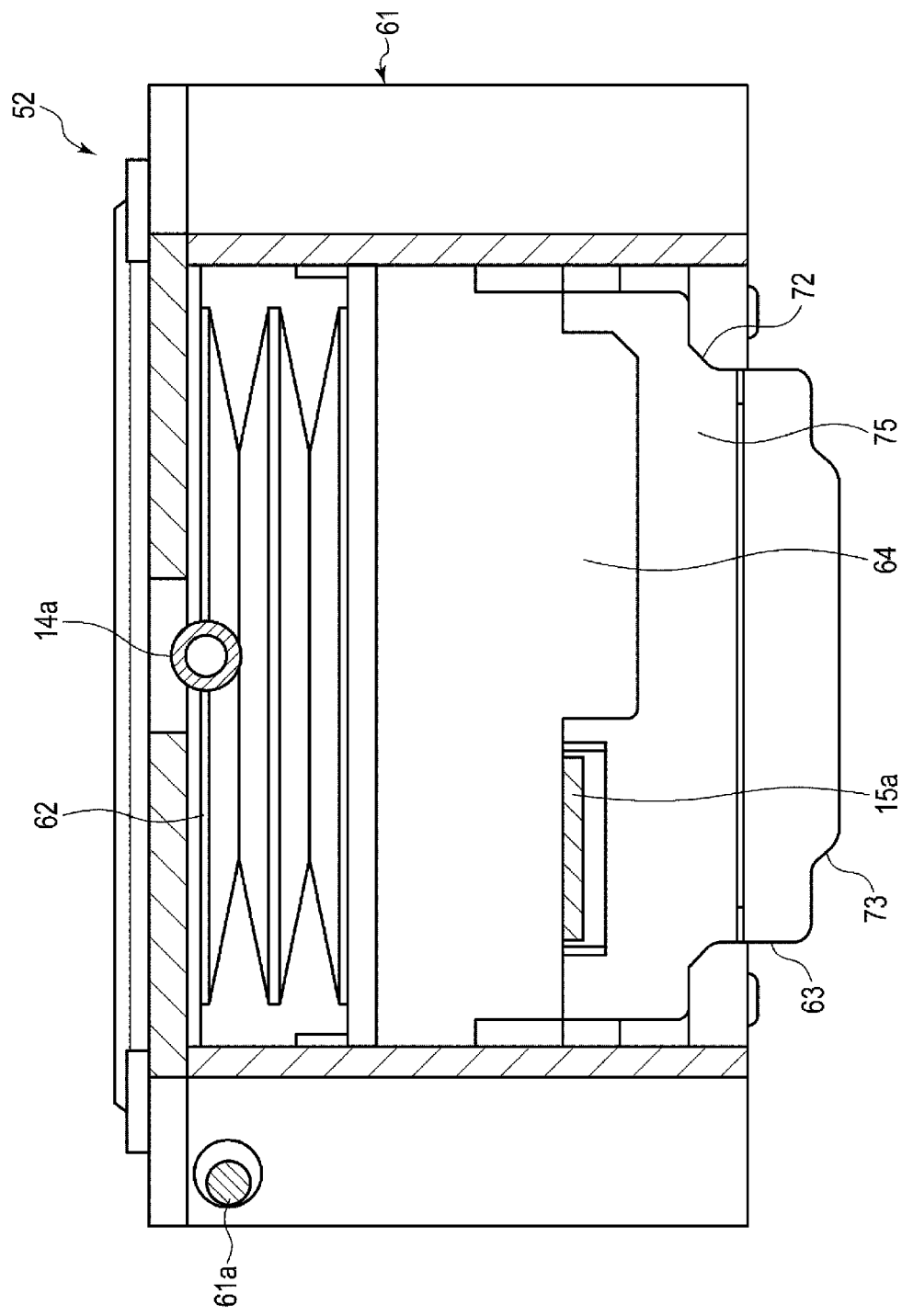

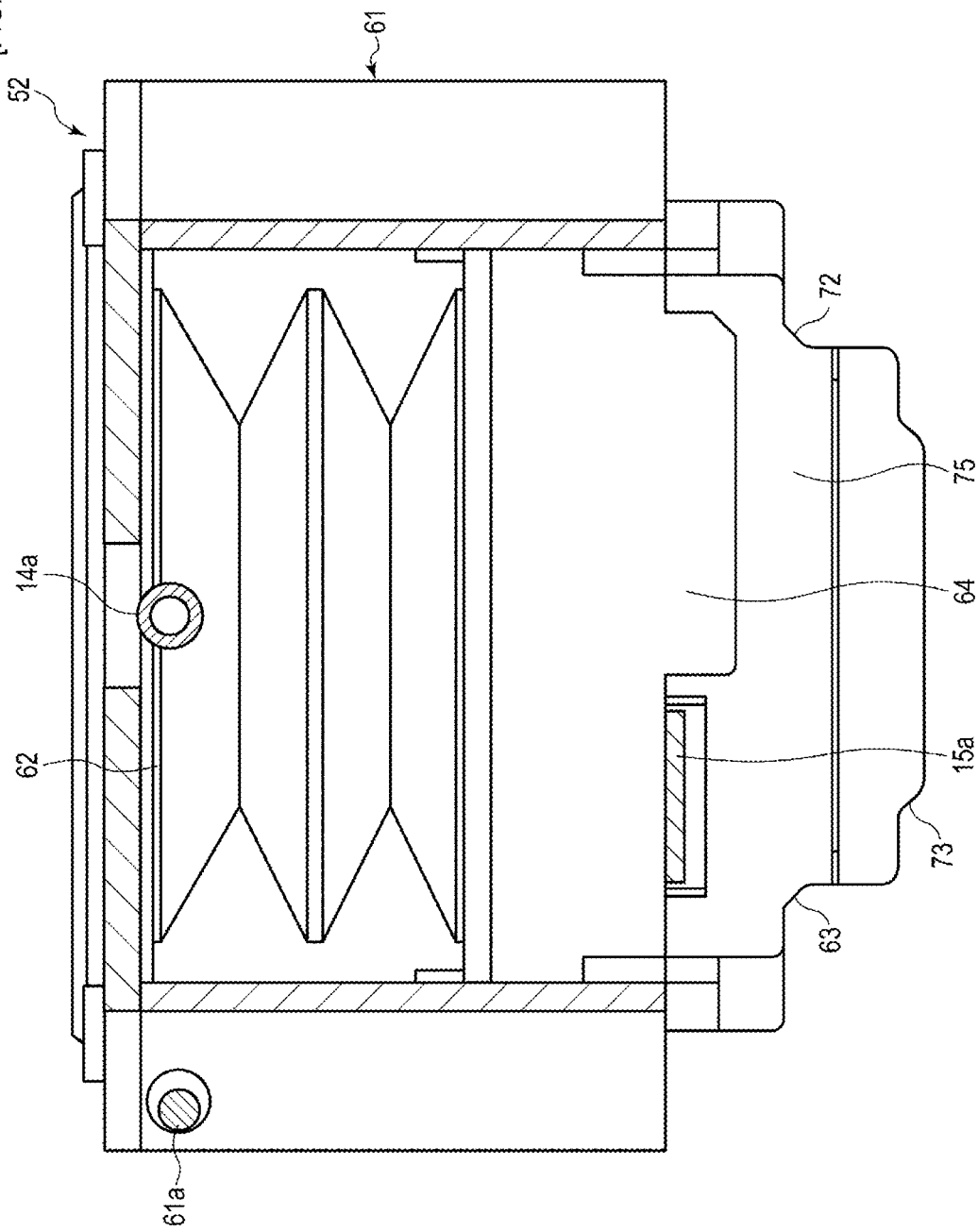

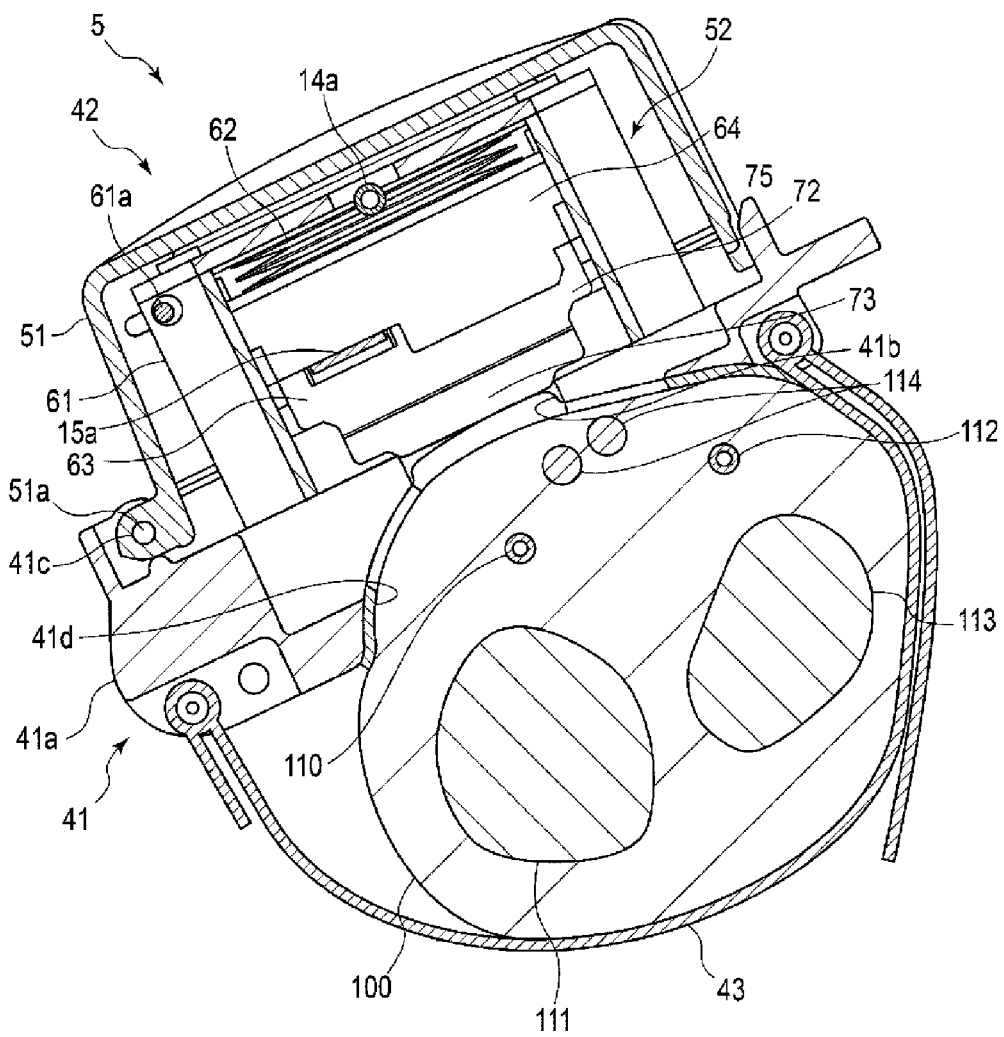
[FIG. 10]

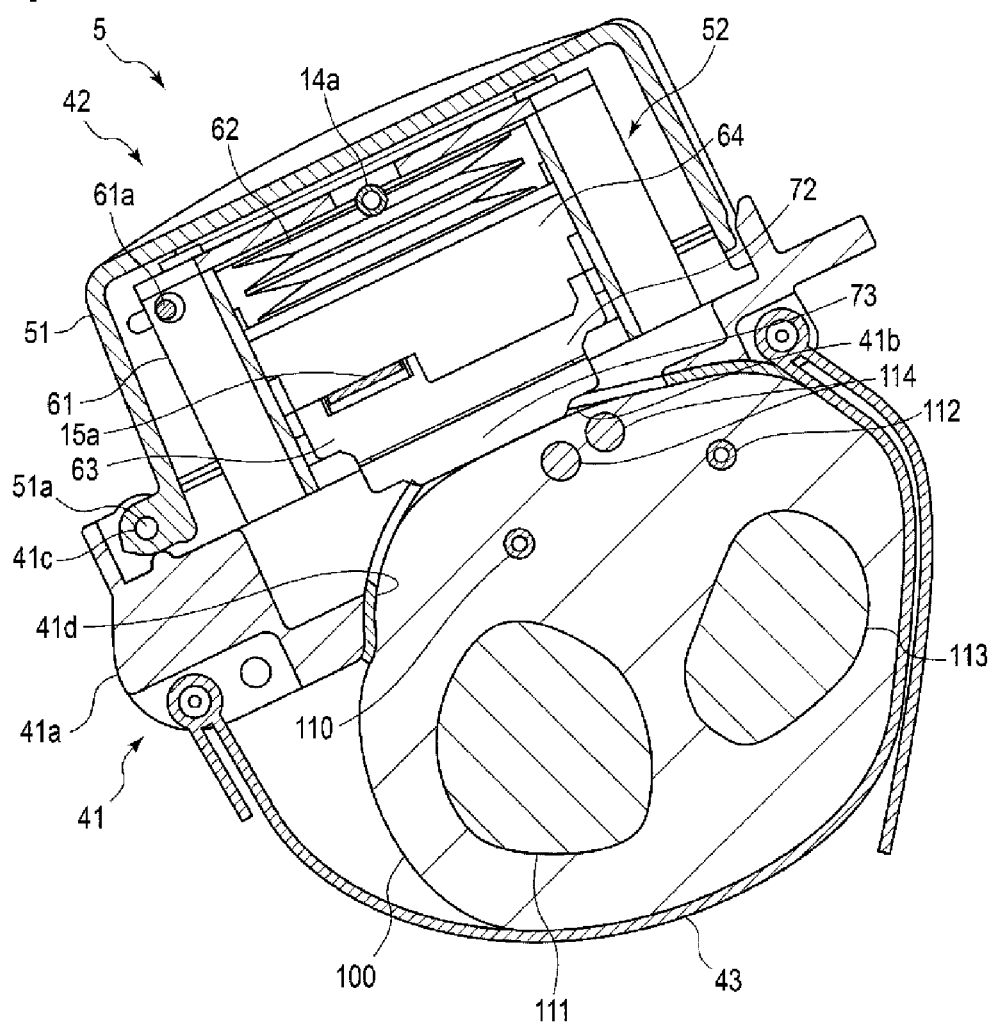
[FIG. 11]

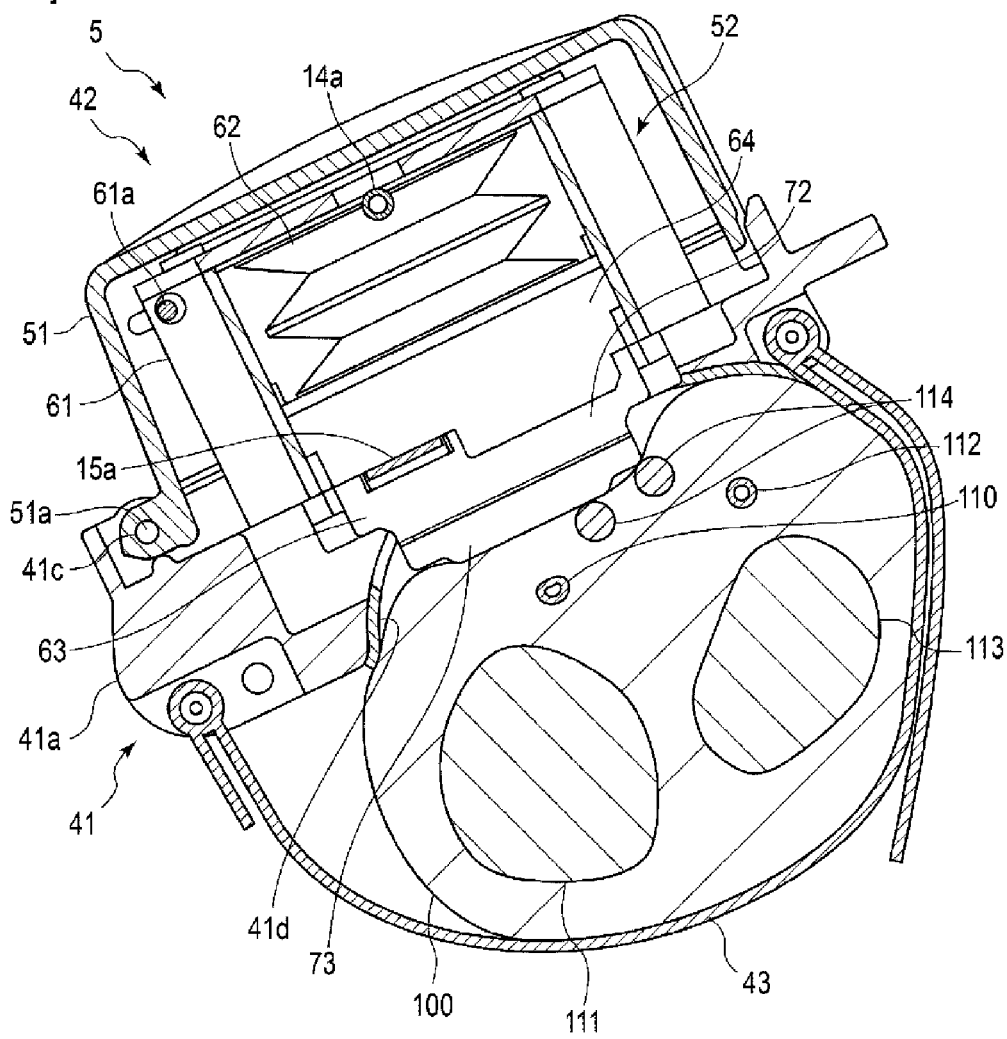
[FIG. 12]

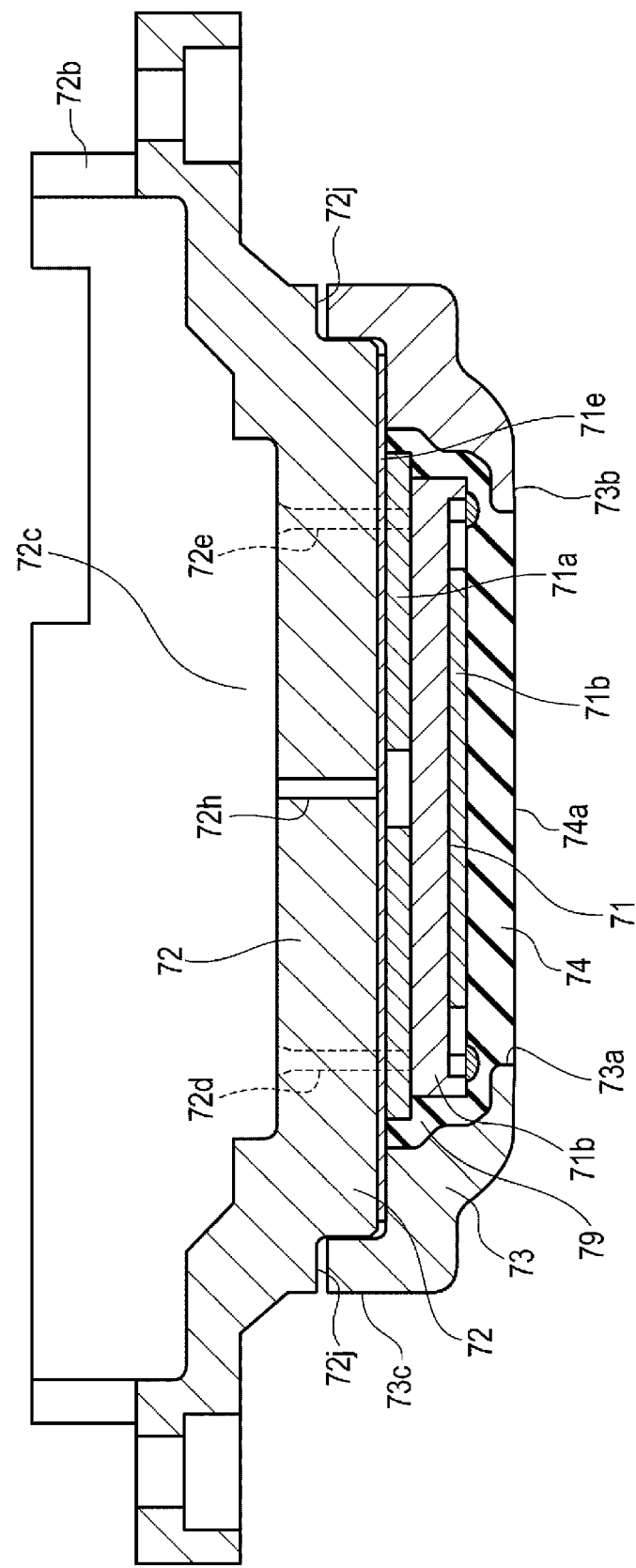
[FIG. 13]

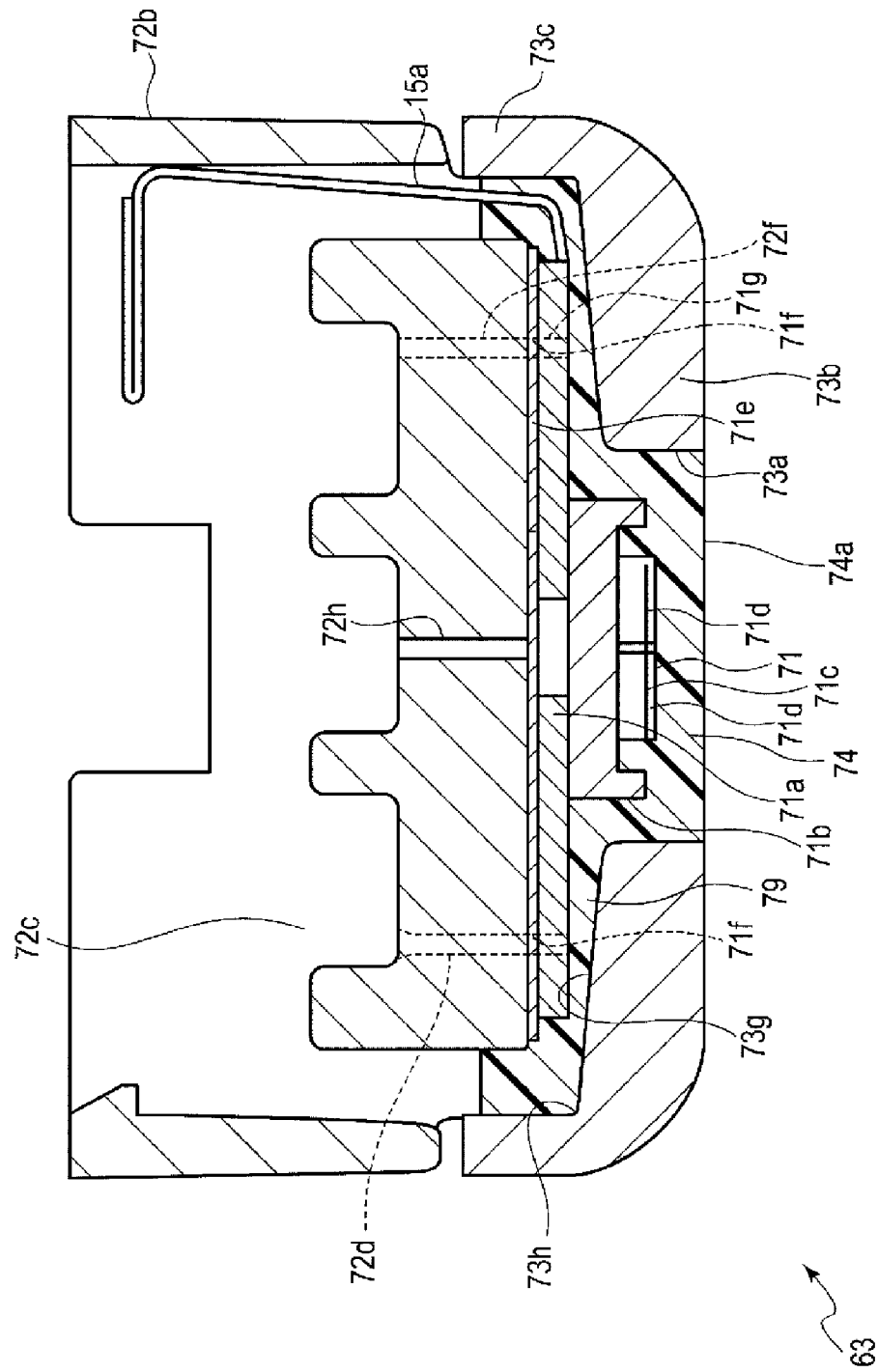
[FIG. 14]

[FIG. 15]
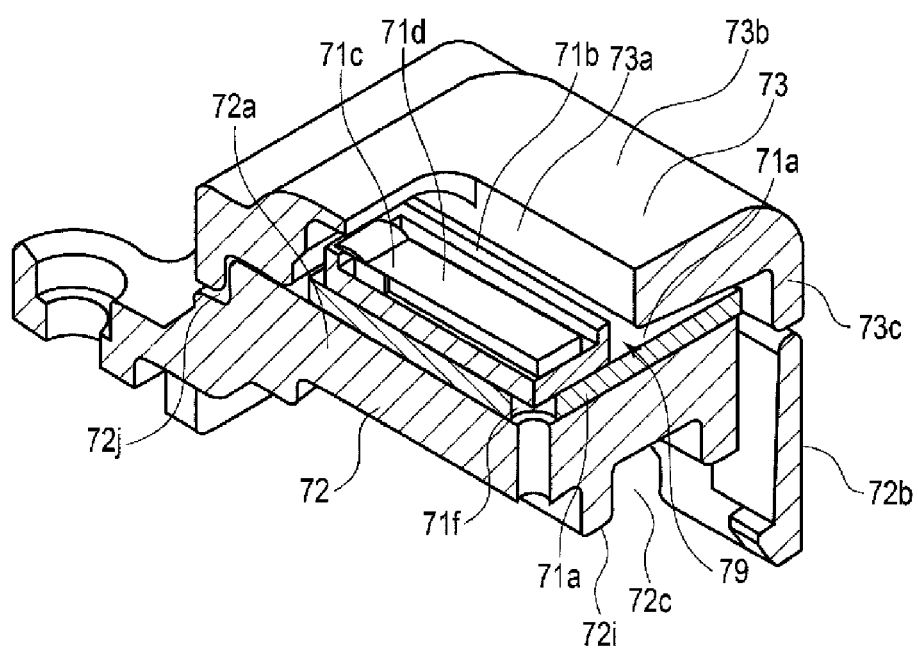

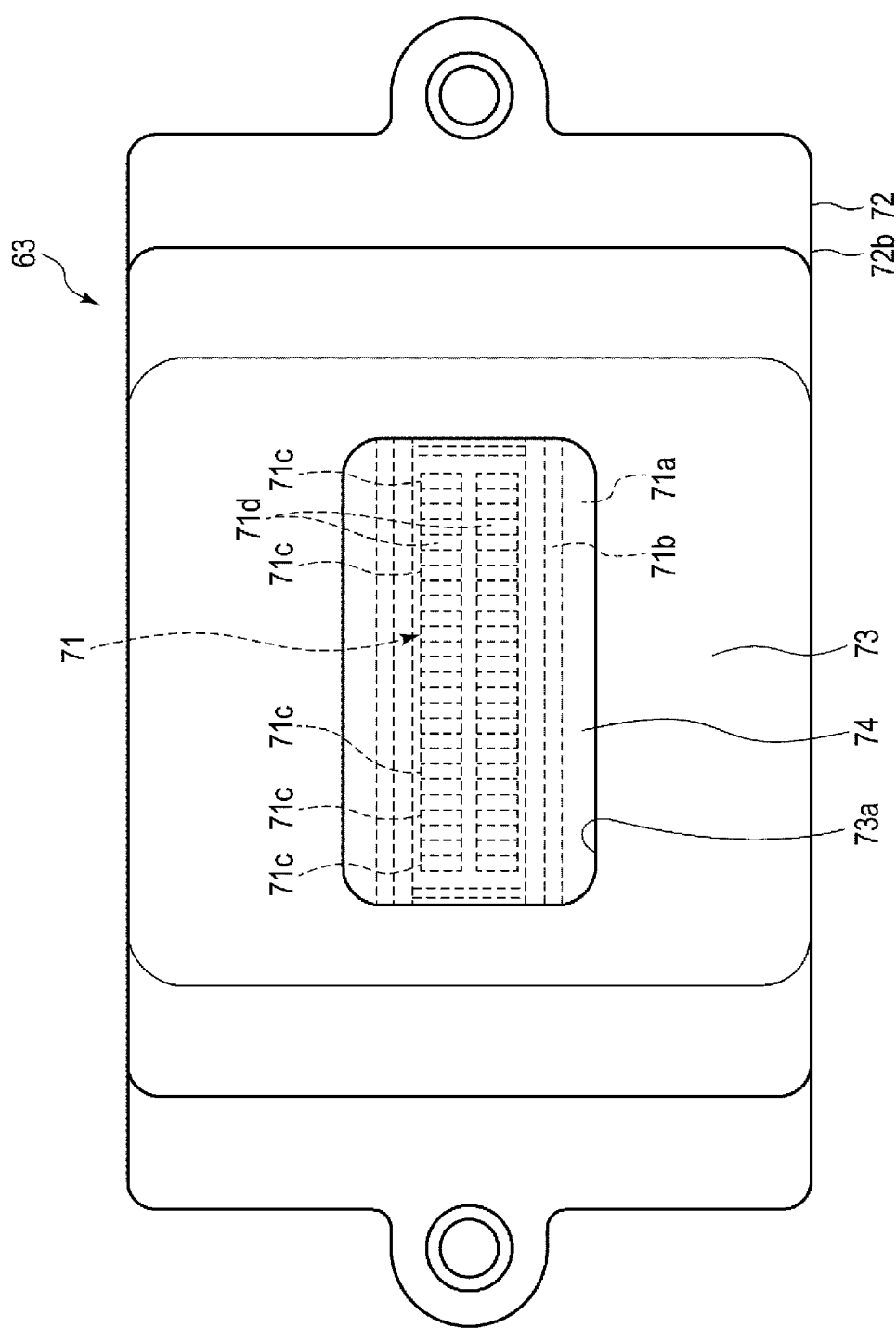

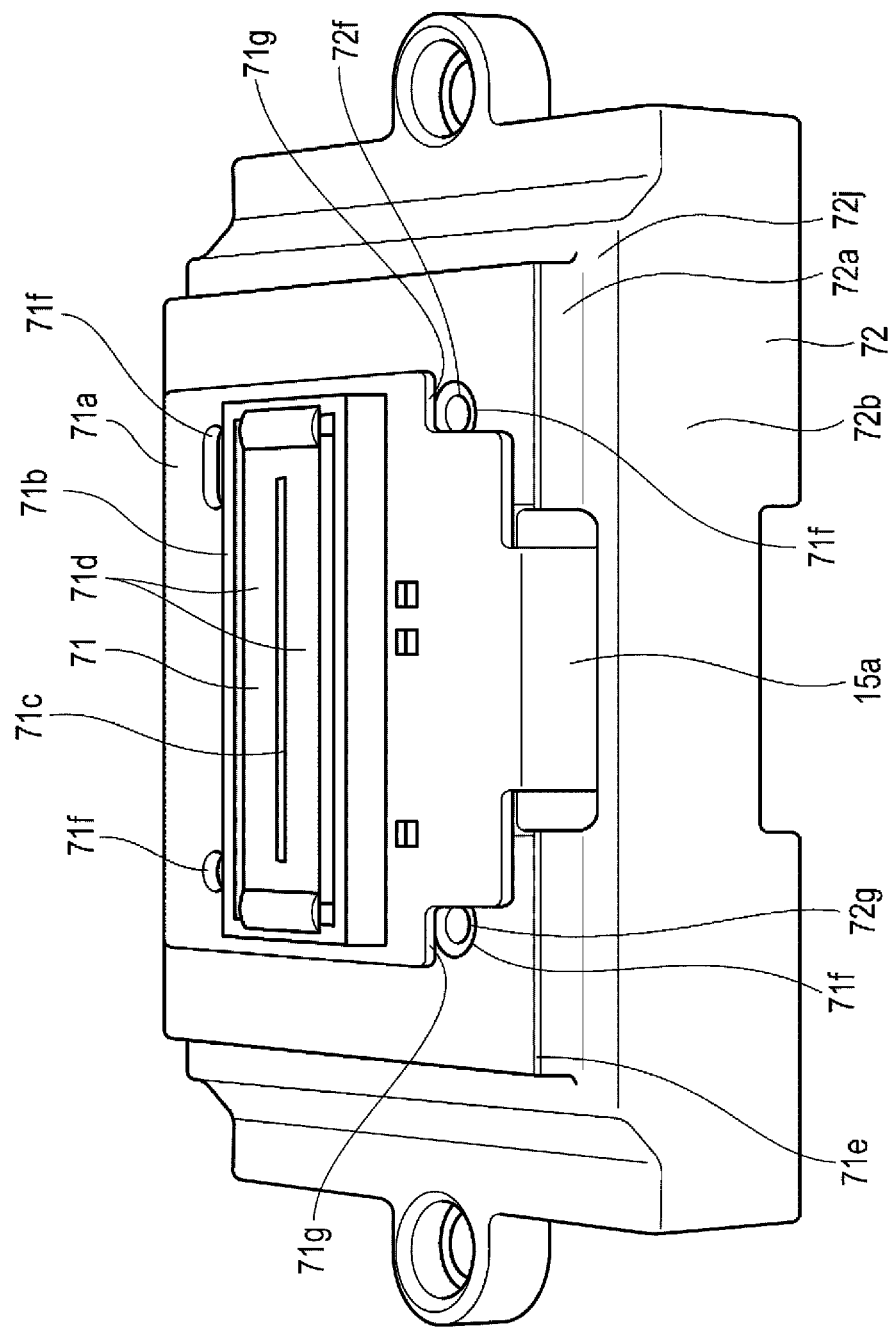
[FIG. 17]

[FIG. 18]
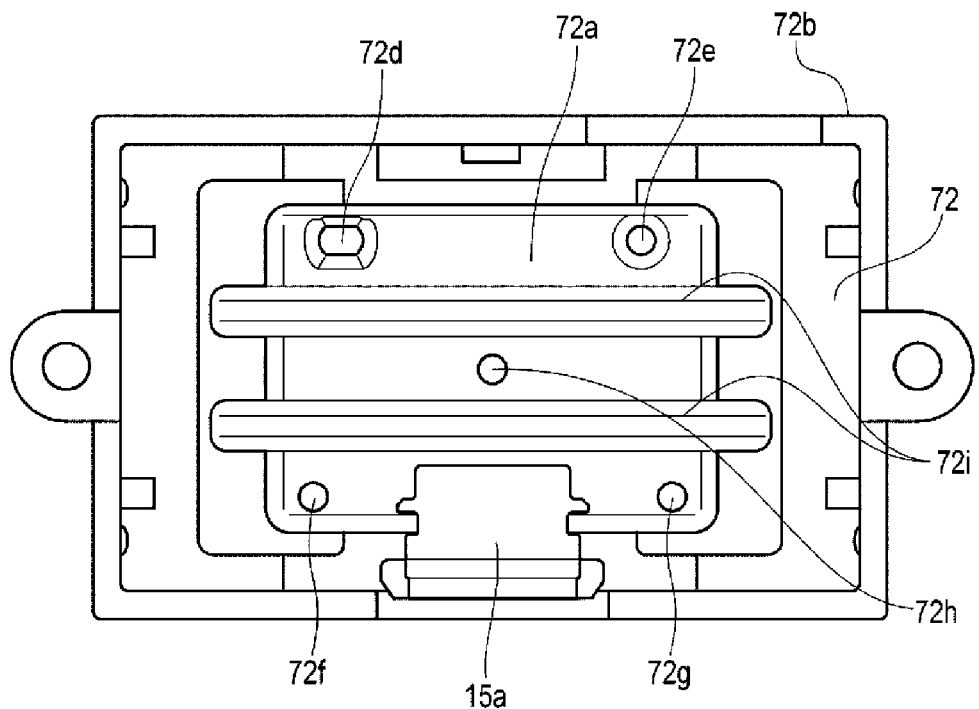
[FIG. 19]
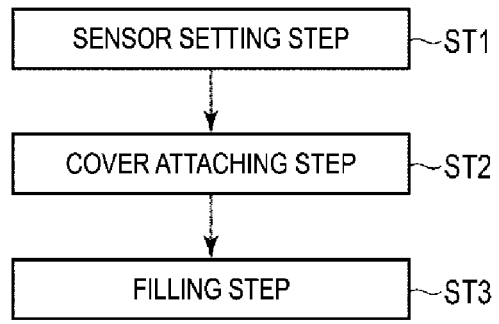

[FIG. 20]
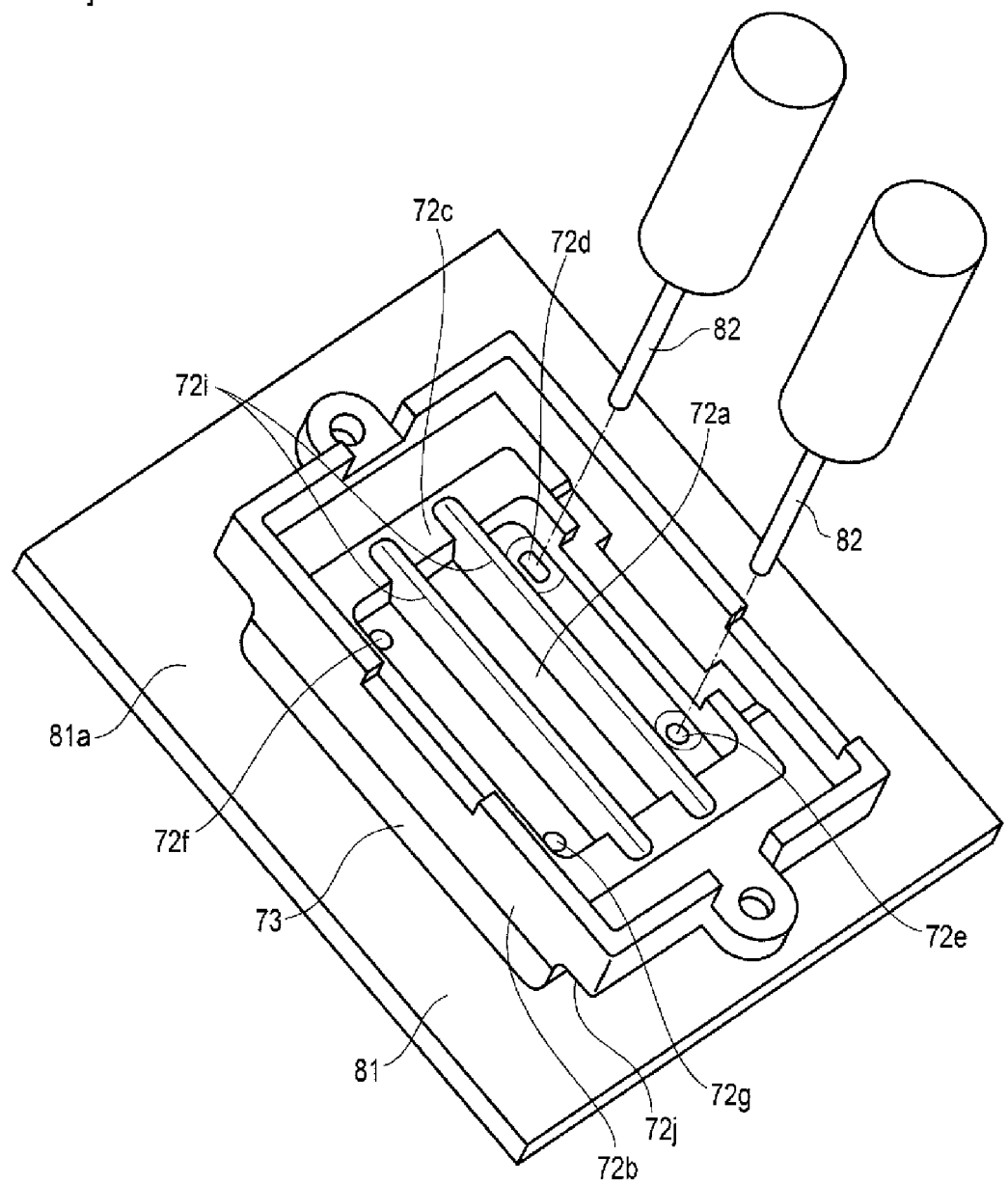

[FIG. 21]
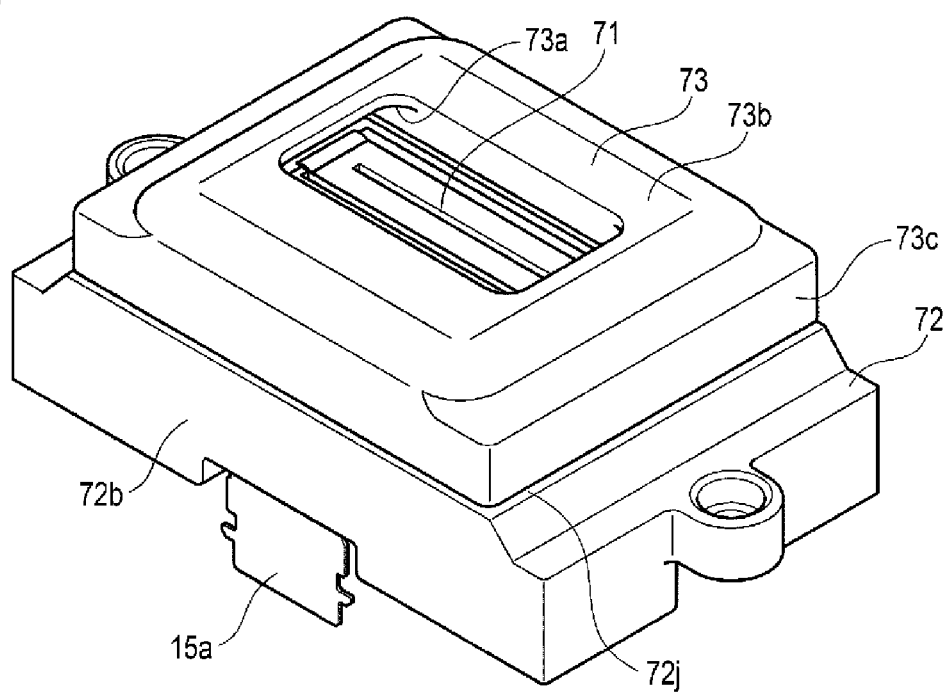

[FIG. 22]
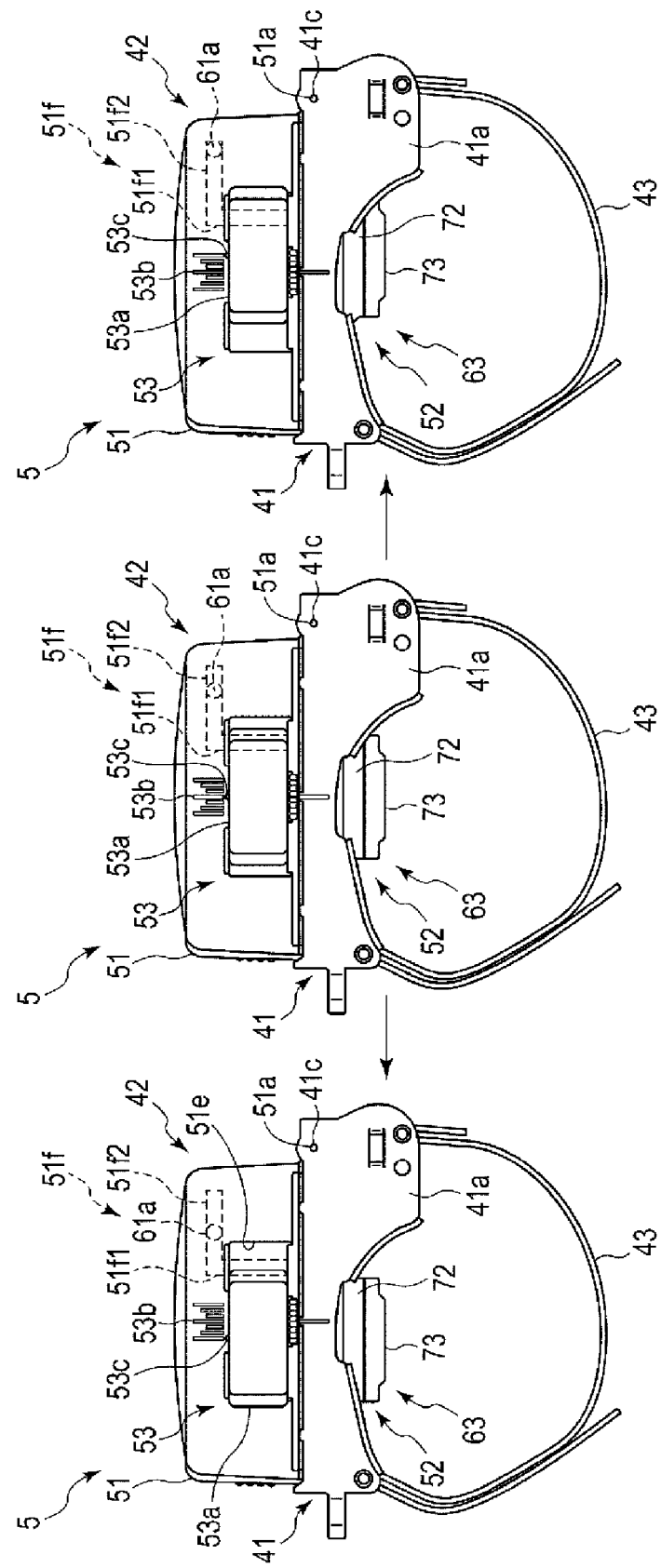

[FIG. 23]
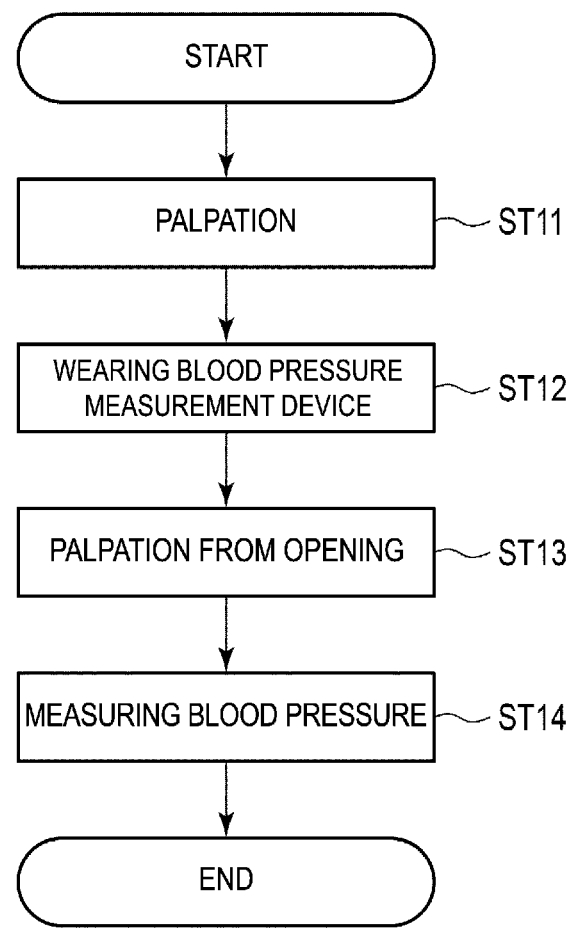

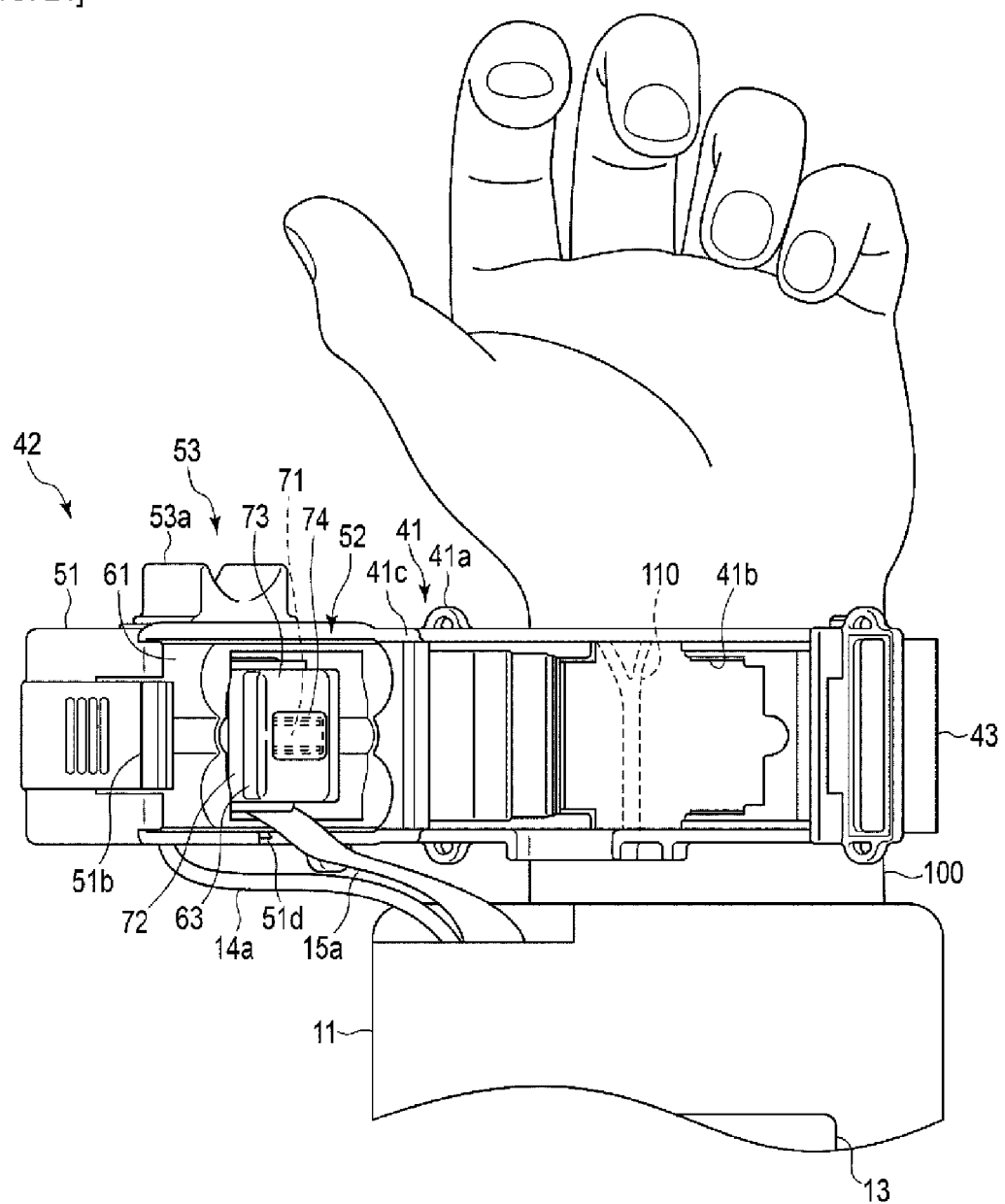
[FIG. 24]

[FIG. 25]
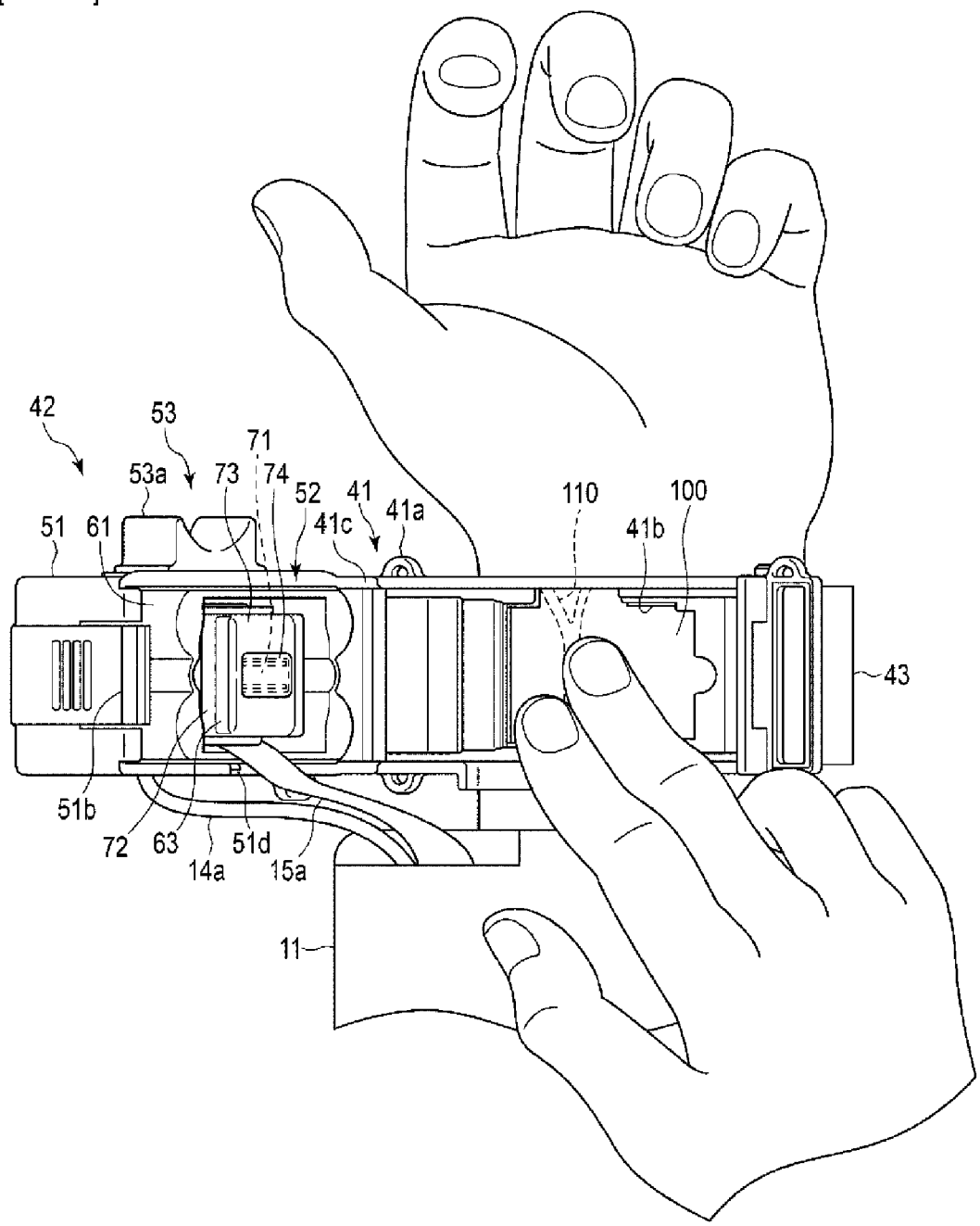

[FIG. 26]
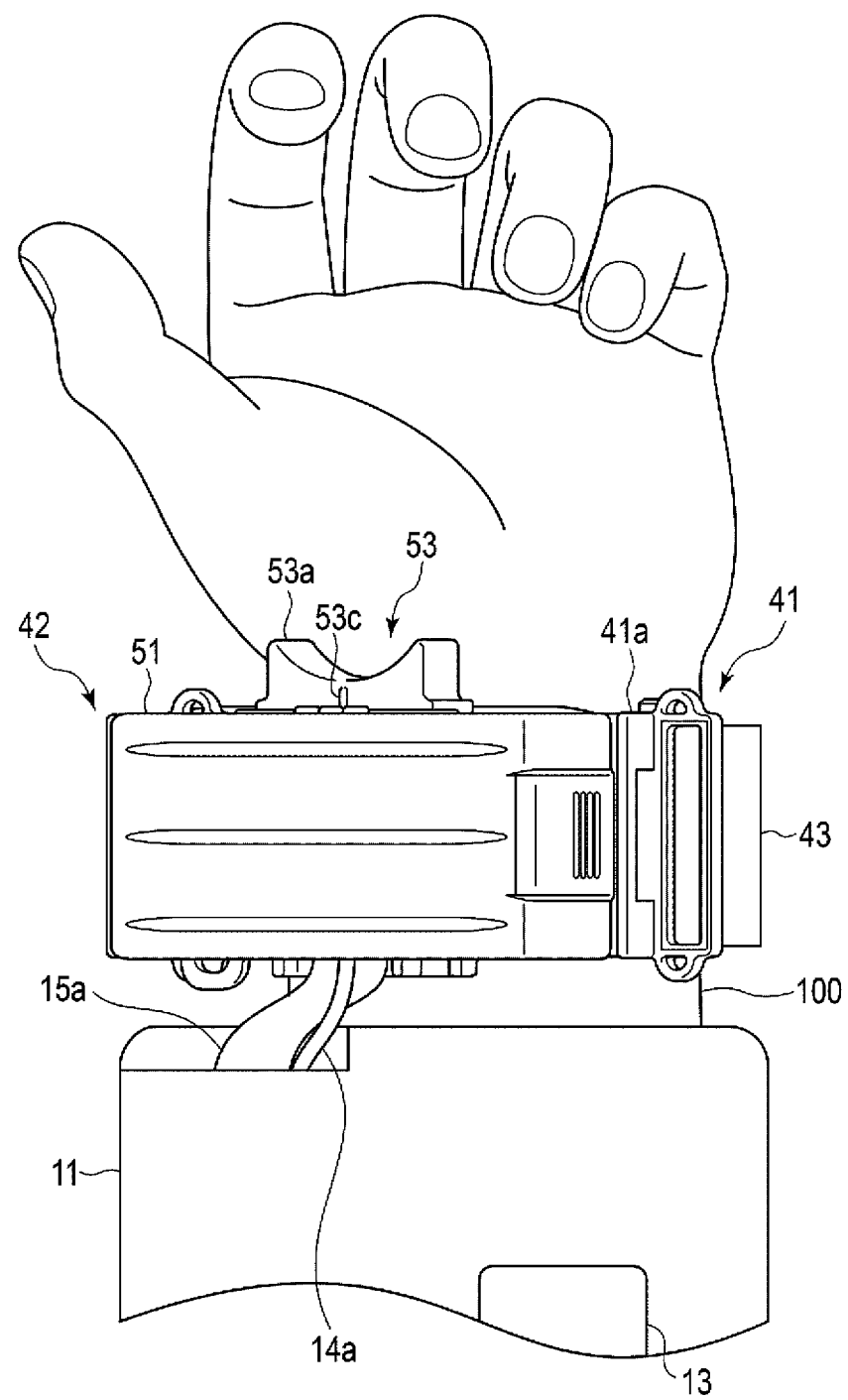

[FIG. 27]
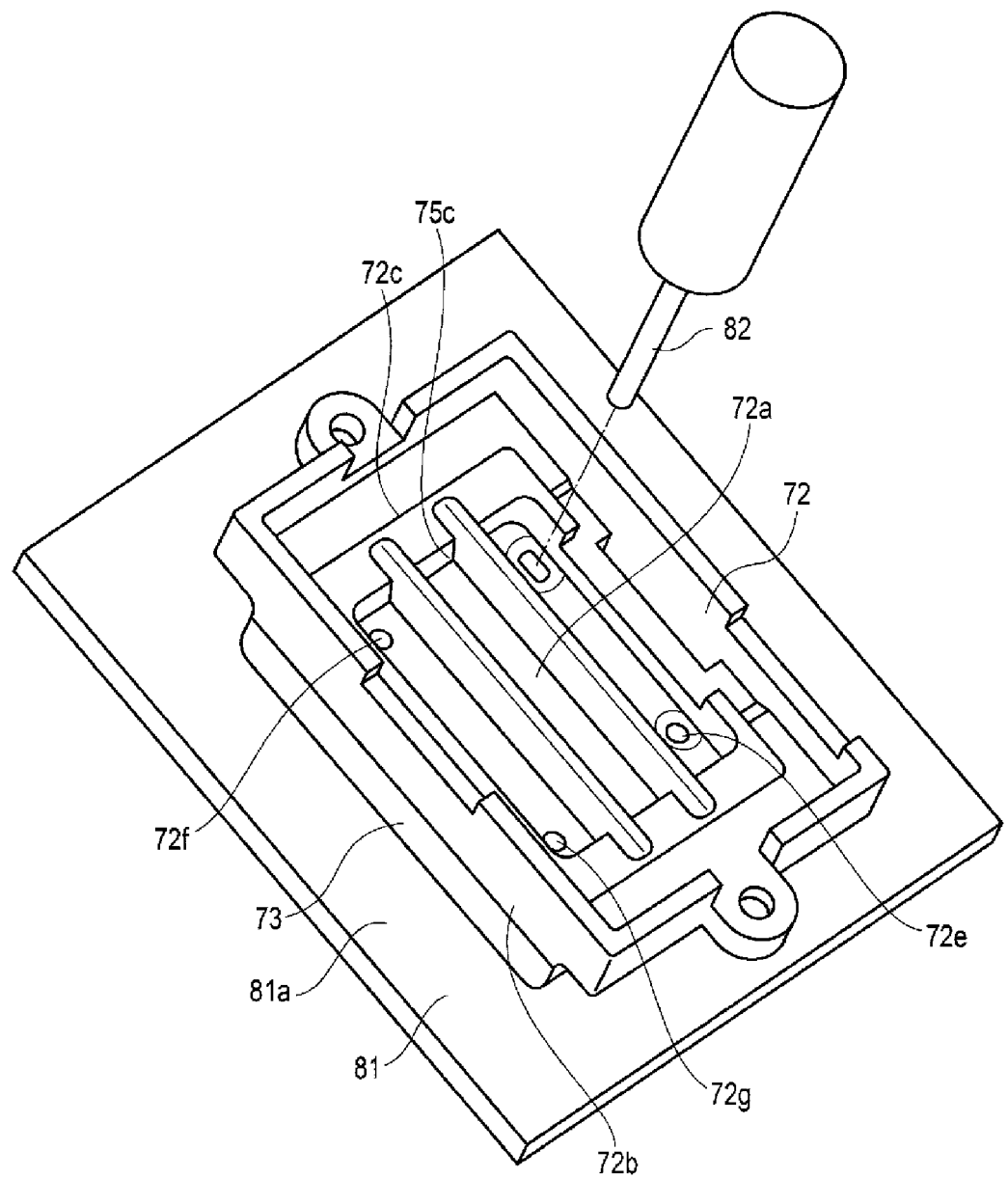

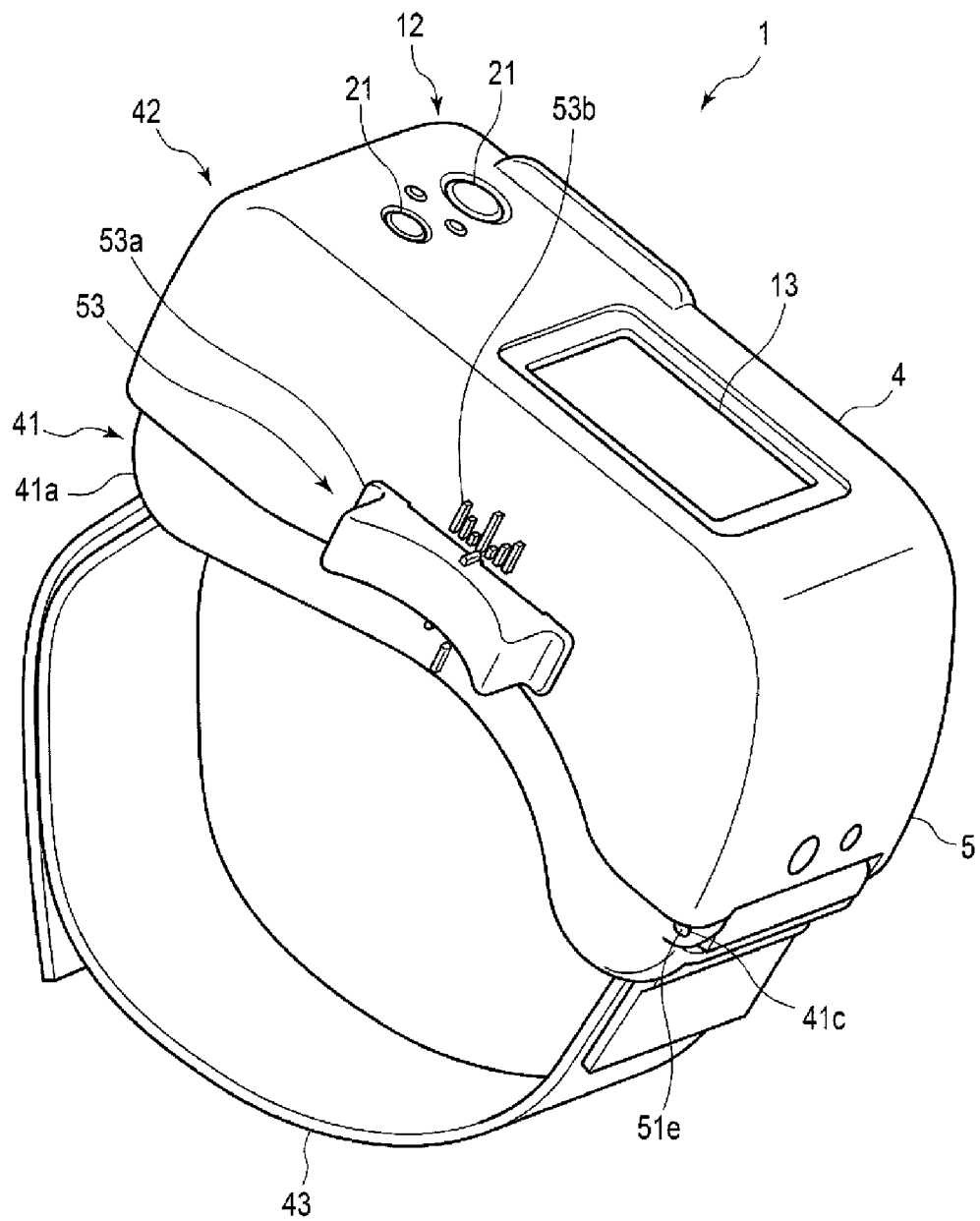
[FIG. 28]

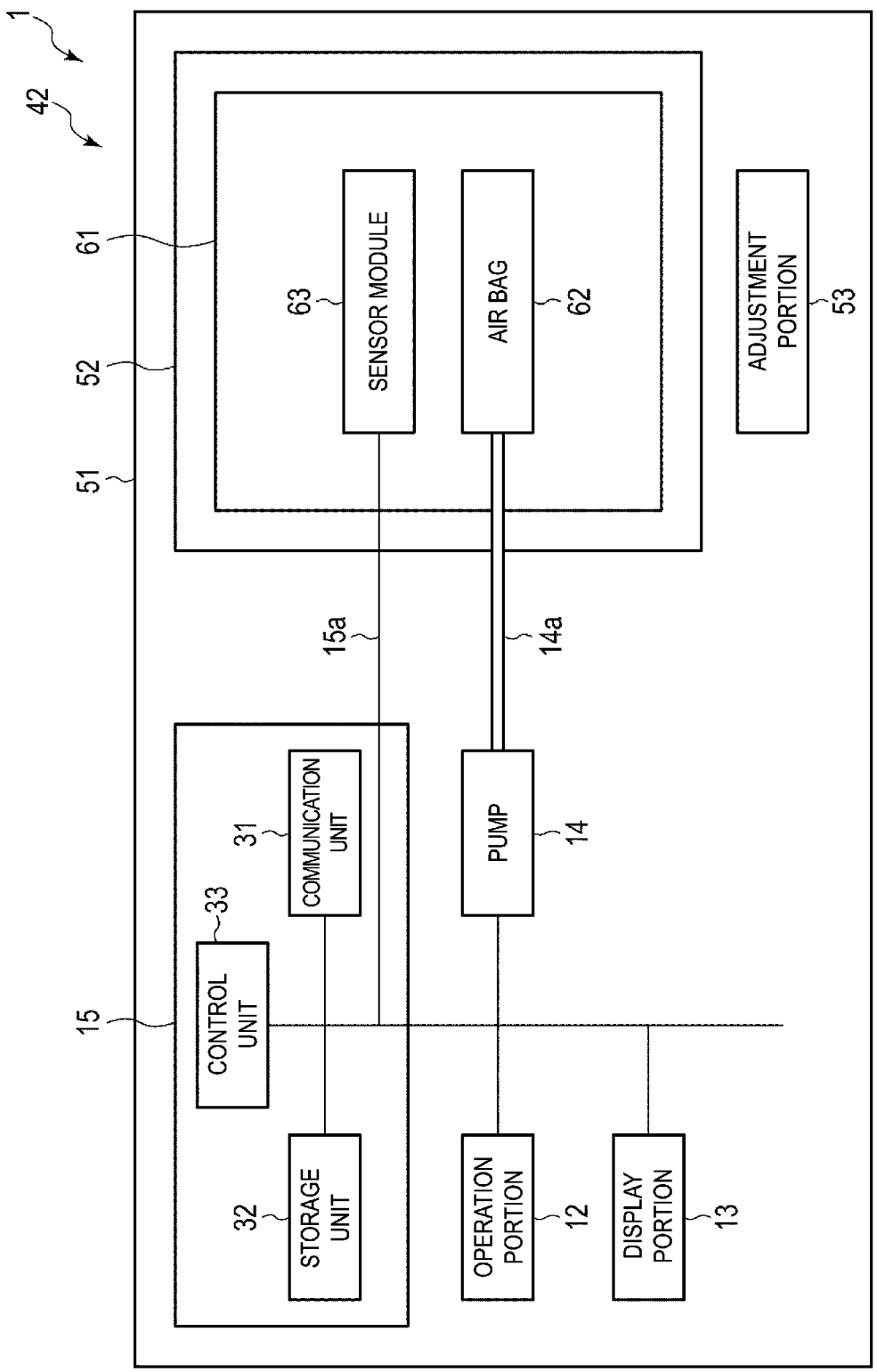
[FIG. 29]

[FIG. 30]
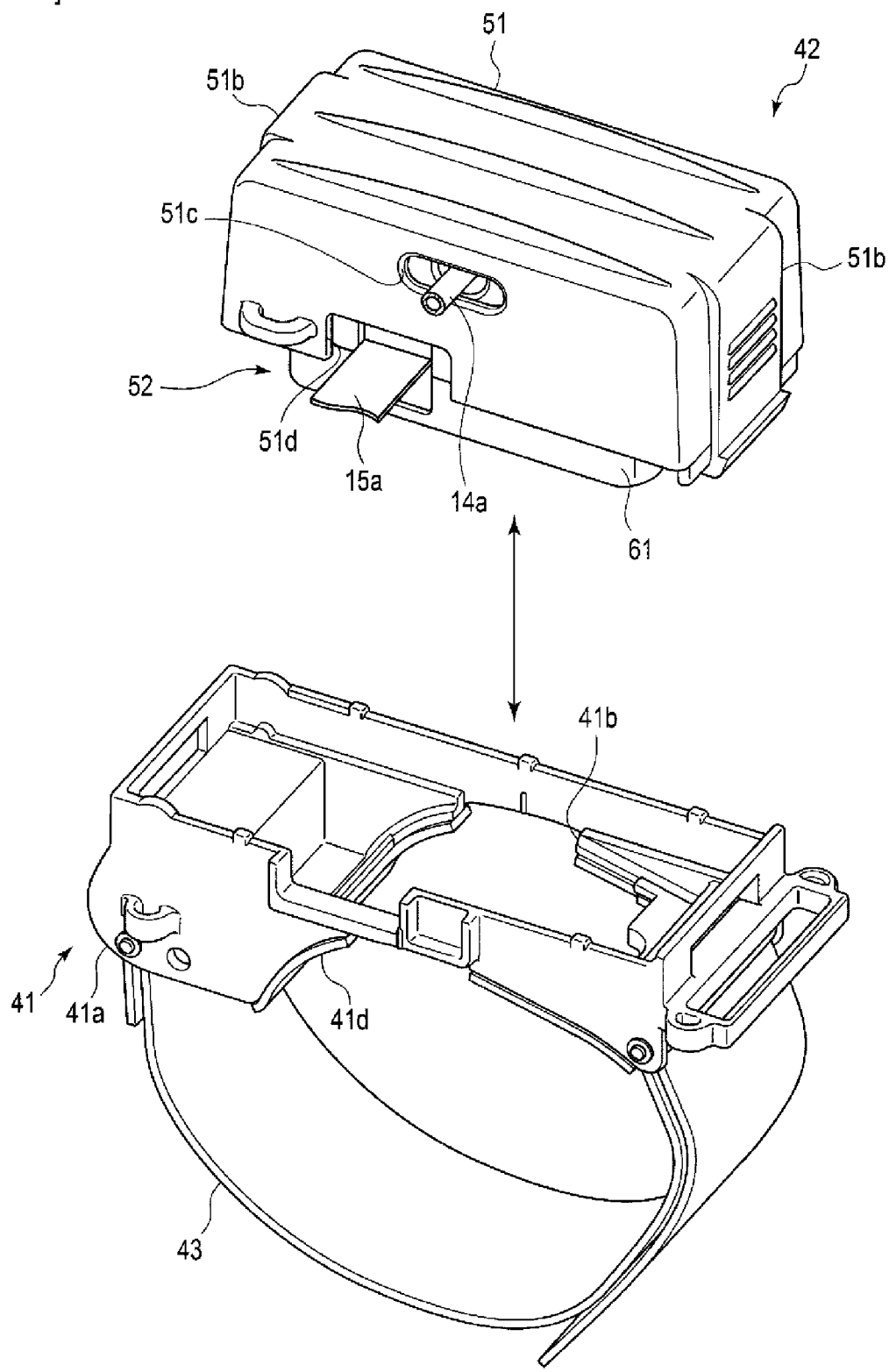

SENSOR MODULE, METHOD FOR MANUFACTURING SENSOR MODULE, AND BLOOD PRESSURE MEASUREMENT DEVICE

CROSS REFERENCE TO RELATED APPLICATIONS

This application is the U.S. national stage application filed pursuant to 35 U.S.C. 365(c) and 120 as a continuation of International Patent Application No. PCT/JP2019/020049, filed May 21, 2019, which application claims priority from Japanese Patent Application No. 2018-099715, filed May 24, 2018, which applications are incorporated herein by reference in their entireties.

TECHNICAL FIELD

The present invention relates to a sensor module for measuring blood pressure, a method for manufacturing a sensor module, and a blood pressure measurement device.

BACKGROUND ART

In recent years, blood pressure measurement devices for measuring blood pressure are being used to monitor health status at home, as well as in medical facilities. In such blood pressure measurement devices, for example, known technologies using the oscillometric method and the tonometry method and the like are used (see Patent Document 1, for example). A blood pressure measurement device using the oscillometric method detects vibration of the artery wall and measures blood pressure by using pressure sensor to detect the pressure of a cuff wrapped around the upper arm or wrist of a living body. A blood pressure measurement device using the tonometry method measures blood pressure by bringing a sensor module including a plurality of pressure sensors into contact with the wrist in a region of the wrist where the artery is found.

CITATION LIST

Patent Literature

Patent Document 1: JP H1-288228 A

SUMMARY OF INVENTION

Technical Problem

In the case in which a pressure sensor is disposed in a sensor module that comes into contact with skin, from the perspective of compatibility with a living body and protecting the pressure sensor, a configuration in which the pressure sensor is covered with resin or the like is employed. The sensor module, for example, is provided with: a sensor base installed with a pressure sensor, a sensor head cover that covers the sensor base and includes an opening at a position opposite the pressure sensor, and a soft portion formed from a soft resin that is disposed in the opening of the sensor head cover and covers the surface of the pressure sensor. In the manufacturing process of the sensor module, the soft portion is formed by injecting a relatively soft resin material such as a silicone resin from the opening of the cover. A known method for forming the soft portion includes: disposing the pressure sensor on the surface of the sensor base, attaching the sensor head cover to the sensor base, and injecting soft resin from the opening of the sensor head cover on the surface side. Because the soft portion comes into direct contact with a living body such as a wrist, the surface of the soft portion needs to be made flat. Thus, when injecting the soft resin from the surface side, a smooth plate is pressed into the opening on the surface side immediately after injection of the resin, and the surface is formed. This complicates the manufacturing process and can cause a decrease in sensor accuracy due to a load acting on the pressure sensor when the smooth plate is pressed.

Thus, an object of the present invention is to provide a sensor module, a method for manufacturing a sensor module, and a blood pressure measurement device, with a highly smooth surface that comes into contact with a sensing target, ensuring high sensor accuracy.

Solution to Problem

According to an aspect, provided is a sensor module including:
  a sensor portion;
  a sensor base including a support wall portion with a flow hole formed extending through the support wall portion from one main surface side to the other main surface side, the sensor portion being disposed on the one main surface side of the sensor base;
  a sensor head cover including an opening at a position opposite the sensor portion and disposed on the one main surface side of the support wall portion of the sensor base with a gap that communicates with the flow hole and the opening formed therebetween; and
  a soft portion disposed in the opening that covers the sensor portion.

According to this aspect, a soft resin can be supplied through the flow hole from the other main surface side of the sensor base opposite the sensor portion. Thus, for example, with the smooth surface disposed in the opening, because the soft resin is filled from the other main surface of sensor base, the process of forming the soft portion is made easy. Accordingly, compared to a process in which the soft resin is filled from the opening side of one main surface and a smooth surface is then pressed against the opening, the process can be simplified and a highly smooth surface can be formed. Additionally, the load on the sensor portion can be reduced, and high sensor accuracy can be ensured.

A sensor module according to the aspect described above may be provided, wherein a plurality of the flow holes are disposed asymmetrically with respect to the sensor portion in an outer circumference of a region where the sensor portion is disposed.

According to this aspect, by disposing the plurality of flow holes in an asymmetric manner, the flow of the soft resin can be set, the soft portion can be reliably filled at the surface of the sensor portion, and a weld line is not formed at a disadvantageous location.

A sensor module according to the aspect described above may be provided, wherein at least one of the flow holes has a different opening area to the other of the flow holes.

According to this aspect, the soft resin can be injected from any of the plurality of flow holes with different opening areas, and air and excess resin can be discharged from the other flow holes, and the flow of the soft resin is easily set.

A sensor module according to the aspect described above may be provided, wherein the sensor portion includes a pressure sensitive element array including one or more pressure sensitive elements;

one or a plurality of the flow holes are formed in both side portions on either side of the pressure sensitive element array that extends in a predetermined first direction; and a sum of opening areas of the flow holes on one side is greater than a sum of opening areas of the flow holes on the other side.

According to this aspect, the soft resin can be injected from the flow hole on the side with the greater opening area, air and excess resin can be discharged from the flow hole on the other side, and the flow of the soft resin can be guided from one direction to the other. Thus, formation of a weld line in a central portion of the sensor portion can be prevented.

A sensor module according to the aspect described above may be provided, wherein a surface of the sensor head cover opposite the sensor base includes an inclined surface inclined toward the opening.

According to this aspect, the soft resin easily flows into the opening via the inclined surface, and the soft portion is easily formed.

According to another aspect, provided is a blood pressure measurement device, including:
the sensor module according to the aspect described above;
a sensing body including: a case that houses the sensor module;
an attach portion including: an opening portion disposed at a position opposite a region where one artery of a wrist is present, the opening portion having a shape that allows the wrist to be palpated, and an end surface that curves conforming to a portion of a shape in a circumferential direction of the wrist; and a fastener provided on the attach portion.

According to this aspect, in a blood pressure measurement device, the sensor module can be easily mounted and the pressure of the artery can be measured at a suitable location.

According to another aspect, provided is a method for manufacturing a sensor module, including disposing a sensor base including a support wall portion with a flow hole formed extending through the support wall portion from one main surface side to the other main surface side, a sensor portion being disposed on the one main surface side of the sensor base and a sensor head cover including an opening at a position opposite the sensor portion opposite one another, with the one main surface side facing downward and with a gap that communicates with the flow hole and the opening formed between the sensor head cover and the one main surface of the sensor base; and supplying a resin material from the other main surface side of at least any one of the flow holes, with an opposing member including a flat surface brought into contact under the sensor head cover, the flat surface of the opposing member closing off the opening.

According to this aspect, with the smooth surface disposed in the opening, because the soft resin is filled from the other main surface of sensor base, the process of forming the soft portion is made easy. Additionally, the soft resin can be injected from any of the inhomogeneously disposed flow holes, allowing the flow of the soft resin to be set. Thus, the soft portion can be reliably filled on the surface of the sensor portion, and a highly smooth surface can be formed. Accordingly, compared to a process in which the soft resin is filled from the opening side of one main surface and a smooth surface is then pressed against the opening, the process can be simplified, the load on the sensor portion can be reduced, and high sensor accuracy can be ensured.

Advantageous Effects of Invention

The present invention provides a sensor module, a method for manufacturing a sensor module, and a blood pressure measurement device, with a highly smooth surface, ensuring high sensor accuracy.

BRIEF DESCRIPTION OF DRAWINGS

FIG. 1 is a perspective view illustrating the configuration of a blood pressure measurement device according to an embodiment of the present invention.

FIG. 2 is a block diagram illustrating the configuration of the blood pressure measurement device.

FIG. 3 is a perspective view illustrating the configuration of a sensor device of the blood pressure measurement device.

FIG. 4 is a perspective view illustrating the configuration of a portion of the sensor device of the blood pressure measurement device.

FIG. 5 is a perspective view illustrating the configuration of a sensor unit of the blood pressure measurement device.

FIG. 6 is a plan view illustrating the configuration of the sensor unit.

FIG. 7 is a cross-sectional view illustrating the configuration of a sensor module and an air bag of the sensor unit.

FIG. 8 is a cross-sectional view illustrating the configuration of the sensor module and the air bag of the sensor unit.

FIG. 9 is a cross-sectional view illustrating the configuration of the sensor module and the air bag of the sensor unit.

FIG. 10 is a cross-sectional view illustrating the configuration of the blood pressure measurement device in a state of being attached to a wrist.

FIG. 11 is a cross-sectional view illustrating the configuration of the blood pressure measurement device in a state of being attached to the wrist.

FIG. 12 is a cross-sectional view illustrating the configuration of the blood pressure measurement device in a state of being attached to the wrist.

FIG. 13 is a cross-sectional view illustrating the configuration of the sensor module of the sensor unit.

FIG. 14 is a cross-sectional view illustrating the configuration of the sensor module.

FIG. 15 is an explanatory diagram illustrating the configuration of a portion of the sensor module.

FIG. 16 is a plan view illustrating the configuration of the sensor module of the sensor unit.

FIG. 17 is a perspective view illustrating the configuration of a portion of the sensor module.

FIG. 18 is a plan view illustrating the configuration of the sensor module.

FIG. 19 is an explanatory diagram illustrating an example of a method for manufacturing the sensor module.

FIG. 20 is an explanatory diagram illustrating a filling step of a method for manufacturing the sensor module.

FIG. 21 is a perspective view illustrating the configuration of the sensor module.

FIG. 22 is an explanatory diagram illustrating the position adjustment of the sensor unit of the blood pressure measurement device.

FIG. 23 is a flowchart illustrating an example of blood pressure measurement using the blood pressure measurement device.

FIG. 24 is an explanatory diagram illustrating an example of blood pressure measurement using the blood pressure measurement device.

FIG. 25 is an explanatory diagram illustrating an example of blood pressure measurement using the blood pressure measurement device.

FIG. 26 is an explanatory diagram illustrating an example of blood pressure measurement using the blood pressure measurement device.

FIG. 27 is an explanatory diagram illustrating a method for manufacturing a sensor module of a blood pressure measurement device according to another embodiment of the present invention.

FIG. 28 is a perspective view illustrating the configuration of a blood pressure measurement device according to another embodiment of the present invention.

FIG. 29 is a block diagram illustrating the configuration of the blood pressure measurement device.

FIG. 30 is a perspective view illustrating the configuration of a blood pressure measurement device according to another embodiment of the present invention.

DESCRIPTION OF EMBODIMENTS

FIG. 1 is a perspective view illustrating the configuration of the blood pressure measurement device 1 according to an embodiment of the present invention in a state in which a body fastener 16 is closed. FIG. 2 is a block diagram illustrating the configuration of the blood pressure measurement device 1. FIG. 3 is a perspective view illustrating the configuration of a sensor device 5 of the blood pressure measurement device 1 in a state in which a sensing body 42 is open. FIG. 4 is a perspective view illustrating the configuration of the blood pressure measurement device 1 with a sensor unit 52 removed from the sensor device 5. FIG. 5 is a perspective view illustrating the configuration of the sensor unit 52 of the blood pressure measurement device 1. FIG. 6 is a plan view illustrating the configuration of the sensor unit 52. FIG. 7 is a cross-sectional view illustrating the configuration of a sensor module 63 and an air bag 62 of the sensor unit 52 taken along a cross-section line VII-VII in FIG. 6. FIG. 8 is a cross-sectional view illustrating the configuration of the sensor module 63 and the air bag 62 taken along a cross-section line VIII-VIII in FIG. 6. FIG. 9 is a cross-sectional view illustrating the configuration of the sensor module 63 and the air bag 62 taken along a cross-section line IX-IX in FIG. 6. FIGS. 10 to 12 are cross-sectional views illustrating the configuration of the blood pressure measurement device 1 in a state of being attached to a wrist 100. FIGS. 13 and 14 are cross-sectional views illustrating the configuration of the sensor module 63 of the sensor unit 52. FIG. 15 is an explanatory diagram illustrating the configuration of a portion of the sensor module 63. FIG. 16 is a plan view illustrating the configuration of the sensor module 63.

Note that in the drawings, a radial artery of a wrist 100 is denoted as 110, a radius is denoted as 111, an ulnar artery is denoted as 112, an ulna is denoted as 113, and a tendon is denoted as 114.

The blood pressure measurement device 1 is an electronic blood pressure measurement device that is attached to the wrist 100 of a living body and calculates a blood pressure value from the pressure of the radial artery 110. As illustrated in FIGS. 1 to 16, the blood pressure measurement device 1 includes a device body 4 and the sensor device 5. For example, the blood pressure measurement device 1 has a configuration in which the sensor device 5 is attached to a region of the wrist 100 where the radial artery 110 is found and in which the device body 4 is attached to the wrist 100 adjacent to the sensor device 5 on the elbow side.

The blood pressure measurement device 1, by pressing the radial artery 110 with the sensor device 5, measures the pressure of the pressure pulse wave per heart beat that changes in conjunction with the heart rate of the radial artery 110, executes, via the device body 4, processing based on the tonometry method on the measured pressure, and obtains the blood pressure.

As illustrated in FIGS. 1 and 2, the device body 4 includes: a body case 11, an operation portion 12, a display portion 13, a pump 14, a control board 15, and the body fastener 16. Also, for example, the device body 4 may be provided with a cuff on the body fastener 16 that is configured to compress the wrist 100 during blood pressure measurement.

The body case 11 houses: a portion of the operation portion 12, a portion of the display portion 13, and the control board 15 and exposes: a portion of the operation portion 12 and a portion of the display portion 13 from the outer surface. In addition, the body fastener 16 is attached to the body case 11.

The operation portion 12 is configured to receive an instruction input from a user. For example, the operation portion 12 includes: a plurality of buttons 21 provided on the body case 11 and a sensor that detects operation of the buttons 21. Note that the operation portion 12 may be provided on the display portion 13 as a touch panel. When operated by the user, the operation portion 12 converts an instruction into an electrical signal. The sensor that detects operation of the buttons 21 is electrically connected to the control board 15 and outputs an electrical signal to the control board 15.

The display portion 13 is disposed in the body case 11 and is exposed from the outer surface of the body case 11. The display portion 13 is electrically connected to the control board 15. The display portion 13 is, for example, a liquid crystal display or an organic electroluminescent display. The display portion 13 displays various information including measurement results such as date and time; blood pressure values like maximum blood pressure and minimum blood pressure; heart rate; and the like.

The pump 14 is, for example, a piezoelectric pump. The pump 14 includes a tube 14a connected to the sensor device 5 for compressing air and supplying compressed air to the sensor device 5 via the tube 14a. The pump 14 is electrically connected to the control board 15.

As illustrated in FIG. 2, the control board 15 includes a communication unit 31, a storage unit 32, and a control unit 33, for example. The control board 15 is configured by the communication unit 31, the storage unit 32, and the control unit 33 being mounted on the board. Also, the control board 15 is connected to the sensor device 5 via a cable 15a. The cable 15a runs from inside the body case 11 to outside the body case 11 via a portion of the outer surface of the body case 11. For example, the cable 15a runs from inside the body case 11 to the sensor device 5 via an opening formed in a side surface of the body case 11.

The communication unit 31 is configured to transmit and receive information from an external device wirelessly or via a wire. The communication unit 31 transmits information, such as information controlled by the control unit 33, measured blood pressure values, pulse, and the like, to an external device via a network and receives a program for software update or the like from an external device via a network and sends this to the control unit.

In the present embodiment, the network is, for example, the Internet, but no such limitation is intended. The network may be a network such as a Local Area Network (LAN)

provided in a hospital or may be a direct wired communication with an external device, using a cable or the like including terminals of a predetermined protocol such as USB. Thus, the communication unit 31 may include a plurality of wireless antennas, micro-USB connectors, or the like.

The storage unit 32 pre-stores: program data for controlling the entire blood pressure measurement device 1; settings data for configuring various functions of the blood pressure measurement device 1; calculation data for calculating blood pressure values and pulse from the pressure measured by pressure sensitive elements 71*c*; and the like. Furthermore, the storage unit 32 stores information such as: the calculated blood pressure value; pulse; time series data in which this calculated data and time are associated; and the like.

The control unit 33 is composed of, for example, a single or a plurality of central processing units (CPU), controls the operation of the entire blood pressure measurement device 1, and executes each processing on the basis of the program data. The control unit 33 is electrically connected to the operation portion 12, the display portion 13, the pump 14, and the sensor device 5, controls the operation of each configuration, transmits and receive signals, and supplies power.

The body fastener 16 includes, for example, one or a plurality of band-like bands; and a fixing member such as a hook-and-loop fastener that secures the band wrapped around the wrist 100. The body fastener 16 fixes the body case 11 to the wrist 100.

With the device body 4 having such a configuration, by the control unit 33 executing processing using the program data stored in the storage unit 32, blood pressure data can be continuously generated from the pulse waves of the radial artery 110 detected by the sensor device 5. The blood pressure data includes data of blood pressure waveforms corresponding to the waveforms of measured pulse waves. The blood pressure data may further include time series data of a blood pressure feature value (blood pressure value). The blood pressure feature value includes, for example and without limitation, systolic blood pressure (SBP) and diastolic blood pressure (DBP). The maximum value in the pulse wave waveform per heart beat corresponds to systolic blood pressure, and the minimum value in the pulse wave waveform of per heart beat corresponds to diastolic blood pressure.

In this embodiment, the device body 4 measures the pressure pulse wave as a pulse wave by the tonometry method. Here, the tonometry method refers to a method for pressing the radial artery 110 from above the skin with appropriate pressure, forming a flat portion in the radial artery 110, and measuring the pressure pulse wave with the sensor device 5 in a balanced state between the interior and the exterior of the radial artery 110. According to the tonometry method, a blood pressure value per heart beat can be acquired.

As illustrated in FIGS. 1, 3, and 4, the sensor device 5 includes: an attach portion 41, the sensing body 42, and a fastener 43.

The attach portion 41 includes a main surface that has a shape that conforms to the circumferential direction of the wrist 100 in the region where the radial artery 110 of the left wrist 100 is found. As a specific example, the attach portion 41 includes a base portion 41*a* that curves conforming to the shape in the circumferential direction of the region in contact with the wrist 100; an opening portion 41*b* formed in the base portion 41*a*; an attachment portion 41*c* provided on the base portion 41*a* for attaching the sensing body 42; and a cushion 41*d* provided on a main surface of the base portion 41*a* that comes into contact with the wrist 100.

The base portion 41*a* is configured to be elongated in one direction. The base portion 41*a* is disposed on a palm side of wrist 100 and on a side portion side on the radius 111 side of the wrist 100, and the main surface disposed on the wrist 100 side curves conforming to the shape in the circumferential direction of the palm side of the wrist 100 and the side portion side on the radius 111 side of the wrist 100. Furthermore, at least the outer circumferential edge side of the main surface of the base portion 41*a* comes into contact with the sensing body 42.

The opening portion 41*b* is provided in a central region of the base portion 41*a* and is formed with a size of one or a plurality of fingers. That is, the opening portion 41*b* is formed with a size that allows the region where the radial artery 110 of the wrist 100 is exposed from the opening portion 41*b* to be palpated by a finger, when the sensor device 5 is attached to the wrist 100, and that allows a portion of the sensing body 42 to come into contact with the wrist 100.

The attachment portion 41*c* is provided on a main surface of the base portion 41*a* opposite the surface facing the wrist 100 and provided on an end side of the base portion 41*a* in the longitudinal direction. The attachment portion 41*c* supports the sensing body 42 and is configured to move the sensing body 42 in a direction away from the base portion 41*a* and a direction toward the base portion 41*a*. As a specific example, the attachment portion 41*c* is a journal-like portion that rotatably journals the sensing body 42 about an axis. For example, the attachment portion 41*c* is integrally formed with the base portion 41*a*.

The cushion 41*d* is, for example, an elastic body configured in a sheet shape from a foaming resin material provided on a main surface of the base portion 41*a* that comes into contact with the wrist 100. The cushion 41*d* protects wrist 100 by elastically deforming, for example, when the blood pressure measurement device 1 is worn on the wrist 100.

As illustrated in FIGS. 2 to 12, the sensing body 42 includes: a case 51, the sensor unit 52, and an adjustment portion 53 for adjusting the position of the sensor unit 52.

The case 51 has a rectangular shape with an open surface opposite the attach portion 41, for example. The case 51 supports the sensor unit 52 and the adjustment portion 53. Furthermore, the case 51 is attached to the attachment portion 41*c* in a manner to be movable back and forth in a direction away from the base portion 41*a*. As a specific example, the case 51 includes a rotation shaft 51*a* rotatably disposed in the attachment portion 41*c*. Also, the case 51 includes an engagement portion 51*b* that fixes the case 51 to the base portion 41*a* when it comes into contact with the base portion 41*a*. The engagement portion 51*b*, for example, is a projection that engages with an opening provided on the base portion 41*a* and, by being operated, is configured to release the engagement with the opening of the base portion 41*a*.

Furthermore, the case 51 includes: a first hole portion 51*c* where the tube 14*a* is disposed, a second hole portion 51*d* where the cable 15*a* is disposed, a third hole portion 51*e* that movably supports a portion of the adjustment portion 53, and a guide groove 51*f* that guides the movement of the sensor unit 52.

The first hole portion 51*c* and the second hole portion 51*d* are provided on the same side wall of the case 51 adjacent to the device body 4 when the device is worn on the wrist 100.

The third hole portion 51e is provided on a side wall opposite to the side wall of the case 51 where the first hole portion 51c and the second hole portion 51d are provided. The third hole portion 51e is a rectangular opening that linearly extends in the longitudinal direction of the case 51, or in other words, the circumferential direction of the wrist 100 when the sensor device 5 is attached to the wrist 100.

The guide groove 51f is provided on the inner surface side of the side wall of the case 51 provided with the third hole portion 51e. The guide groove 51f includes: a first groove 51f1 that extends from an opening end portion of the case 51 to partway toward the ceiling opposite the opening; and a second groove 51f2 that extends in a direction orthogonal to the first groove 51f1. The second groove 51f2 connects to the first groove 51f1 at one end and extends from this end to the other end toward one side in the longitudinal direction of the case 51.

The sensor unit 52 includes: a movable case 61, the air bag 62, the sensor module 63, and a movable base 64 that supports the sensor module 63 to be movable in one direction with respect to the movable case 61. The sensor unit 52 is supported by the case 51 in a manner to be movable in a predetermined range in the longitudinal direction of the case 51 via the adjustment portion 53.

The movable case 61 houses the sensor module 63 and the movable base 64 and supports the movable base 64 supporting the sensor module 63 in a manner allowing the movable base 64 to move toward the opening portion 41b of the attach portion 41. The movable case 61 is supported in a manner to be movable in the longitudinal direction of the case 51 inside the case 51.

As a specific example, the movable case 61 has a rectangular box-like shape with the surface opposite the attach portion 41 housing the air bag 62 and the sensor module 63 being open. The movable case 61 houses the air bag 62, the sensor module 63, and the movable base 64. In the movable case 61, the air bag 62 is disposed between the ceiling and the movable base 64. The movable case 61 supports the movable base 64 in a manner allowing the movable base 64 to move in one direction so that the sensor module 63 can protrude out from the opening of the movable case 61.

The movable case 61 includes: a guide projection 61a disposed on the outer surface of a side wall opposite the side wall on which the guide groove 51f of the case 51 is provided in a manner allowing the guide projection 61a to move in the guide groove 51f; and a fixing portion 61b in which a portion of the adjustment portion 53 is fixed. As the guide projection 61a moves in the second groove 51f2, the movable case 61 moves in the longitudinal direction of the case 51.

The air bag 62 has a bellows-like structure. The air bag 62 is fluidly connected to the pump 14 via the tube 14a. As illustrated in FIGS. 7 to 12, the air bag 62 expands in a direction from the ceiling of the movable case 61 toward the opening. When the air bag 62 expands, the sensor module 63 is moved from a position where the sensor module 63 is housed within the movable case 61 to a position where the sensor module 63 projects from the opening of the movable case 61 and comes into contact with the wrist 100 via the opening portion 41b of the attach portion 41. The air bag 62 is formed from polyurethane, for example. The air bag 62 and the pump 14 together constitute a pressing mechanism that presses the sensor module 63 toward the wrist.

As illustrated in FIGS. 13 to 18, the sensor module 63 includes: the pressure sensor portion 71, the sensor base 72 that supports the pressure sensor portion 71, a sensor head cover 73 that covers the sensor base 72 and includes an opening 73a in a region opposite the pressure sensor portion 71, and a soft portion 74 provided in the opening 73a of the sensor head cover 73. FIG. 17 is a perspective view illustrating the configuration of a portion of the sensor module 63. FIG. 18 is a plan view of the sensor module 63 as viewed from the other side.

The sensor module 63 is disposed inside the movable case 61 and is supported by the movable case 61 in a manner allowing the sensor module 63 to move in a predetermined movement range in the direction of the ceiling and the opening of the movable case 61 opposing one another. In other words, the sensor module 63 is supported in a manner to be movable within the movable case 61, and the movement is restricted by a restriction portion such as a stopper or like when the sensor module 63 moves from the opening of the movable case 61 to the position where the sensor module 63 projects out a certain amount or more.

The pressure sensor portion 71 includes: a flexible substrate 71a, a substrate 71b mounted on the flexible substrate 71a, and a plurality of the pressure sensitive elements 71c mounted on the substrate 71b. The pressure sensor portion 71 is mounted on one main surface of the sensor base 72 and transmits a pressure value measured by the plurality of pressure sensitive elements 71c to the control board 15 via the cable 15a.

The flexible substrate 71a has a rectangular plate-like shape and is adhered on the sensor base 72 via an adhesive sheet 71e. The flexible substrate 71a and the adhesive sheet 71e are provided with an opening 71f and a cutout portion 71g formed at positions overlapping flow holes 72d, 72e, 72f, 72g of the sensor base 72 described below and are formed with a shape that does not close off the flow holes 72d, 72e, 72f, 72g.

A predetermined circuit pattern and the substrate 71b are formed on one main surface of the flexible substrate 71a. The flexible substrate 71a is connected to the cable 15a and is electrically connected to the control board 15 via the cable 15a.

The substrate 71b has a rectangular plate-like shape and supports the plurality of pressure sensitive elements 71c. The substrate 71b and the plurality of pressure sensitive elements 71c constitute a sensor chip.

The plurality of pressure sensitive elements 71c (the pressure sensor) are arranged in one direction, forming a pressure sensitive element array 71d. The plurality of pressure sensitive elements 71c are arranged side by side in one direction along the width direction of the wrist 100 when the device is worn, for example. A single or a plurality of the pressure sensitive element arrays 71d are provided. In the case in which the plurality of the pressure sensitive element arrays 71d are provided, the plurality of pressure sensitive element arrays 71d are disposed at predetermined intervals in a direction orthogonal to the arrangement direction of the plurality of pressure sensitive elements 71c. In the present embodiment, two rows of the pressure sensitive element arrays 71d are disposed. The pressure sensitive elements 71c are electrically connected to the circuit on the flexible substrate 71a.

The sensor base 72 is made from a synthetic resin, for example, includes, integrally, a support wall portion 72a that supports the pressure sensor portion 71 and a circumferential wall portion 72b vertically provided around the outer circumferential edge of the support wall portion 72a on the rear surface side on the opposite side to the living body, and is provided with a recess portion 72c on the rear side of the support wall portion 72a. The sensor base 72 supports the pressure sensor portion 71 and the cable 15a connected to the pressure sensor portion 71.

The support wall portion 72a has a rectangular plate-like shape with a predetermined thickness. The support wall portion 72a, on the surface side, which is the living body side, supports the pressure sensor portion 71 in a region opposite the opening 73a of the sensor head cover 73. A step portion 72j with a projecting central portion is formed in an outer circumferential edge portion of the support wall portion 72a. When the sensor head cover 73 and the sensor base 72 are assembled together, a frame portion 73c engages with the step portion 72j and is placed in position.

The support wall portion 72a includes a plurality of through-holes that extend through in the thickness direction. Specifically, on either side of the pressure sensor portion 71, the first hole 72d and the second hole 72e forming a flow inlet are located in a side portion on one side, and the third hold 72f and the fourth hole 72g forming a flow outlet are located in a side portion on the other side. In other words, the flow holes 72d, 72e, 72f, 72g are disposed in both side portions on either side of the pressure sensitive element arrays 71d.

In the side portion of the support wall portion 72a on one side of the pressure sensor portion 71, the first hole 72d is located at an end in the longitudinal direction of the pressure sensor portion 71, and the second hole 72e is located at the other end. Also, in the side portion of the support wall portion 72a on the other side of the pressure sensor portion 71, the third hole 72f is formed at an end in the longitudinal direction of the pressure sensor portion 71 and the fourth hole 72g is formed at the other end.

The flow holes 72d to 72g are disposed inhomogeneously around the circumference of the region where the pressure sensor portion 71 is disposed. For example, the size and shape of the plurality of flow holes 72d to 72g are different, and the flow path resistance is different. Alternatively, the plurality of flow holes 72d to 72g are disposed in a non-uniform manner. For example, the distance from the pressure sensitive element 71c disposed in the center of the pressure sensor portion 71 is different. In other words, the flow holes 72d to 72g have an asymmetric configuration with respect to the pressure sensitive element array 71d of the pressure sensor portion 71.

Because the plurality of flow holes 72d to 72g extend through the support wall portion 72a in the thickness direction, the soft resin material that forms the soft portion 74 described below can flow from the other main surface side to the opening 73a on the one main surface side. At least one of the hole portions of the plurality of flow holes 72d to 72g serves as a flow inlet for the soft resin material, and the other hole portions serve as flow outlets through which excess resin material and air are discharged during filling with the soft resin material. In the present embodiment, as an example, the first hole 72d and the second hole 72e are inflow holes, and the other two holes, the third hole 72f and the fourth hole 72g are outflow holes.

The first hole 72d is formed in an elliptical shape elongated in the first direction, with the dimension of the opening in the longitudinal direction of the pressure sensor portion 71 being greater than the dimension of the opening in the width direction of the pressure sensor portion 71. The first hole 72d is formed with a greater opening area than the other three holes 72e, 72f, 72g. Furthermore, the inner wall of the first hole 72d is formed with a tapered shape with the opening diameter on the rear side increasing.

The second hole 72e has a circular shape. The second hole 72e is formed with a smaller opening area than the first hole 72d. Furthermore, the inner wall of the second hole 72e is formed with a tapered shape with the opening diameter on the rear side increasing. The second hole 72e has the same flow path diameter as the third hole 72f and the fourth hole 72g and is formed with a tapered shape with an opening area on the rear side being greater than that of the third hole 72f and the fourth hole 72g.

The third hole 72f and the fourth hole 72g have a circular shape with a smaller opening diameter than the first hole 72d and the second hole 72e. Additionally, the third hole 72f and the fourth hole 72g are formed to be constant in the axial direction of the hole portion, that is, in the thickness direction of the support wall portion 72a.

The third hole 72f and the fourth hole 72g are disposed spaced apart, and the interval between the third hole 72f and the fourth hole 72g in the first direction is set to be greater than the interval between the first hole 72d and the second hole 72e.

Thus, the sum of the opening areas of the first hole 72d and the second hole 72e disposed in the side portion on one side of the pressure sensor portion 71 is greater than the sum of the opening areas of the holes 72f and 72g disposed in the side portion on the other side of the pressure sensor portion 71.

A fifth hole 72h is a circular hole that extends through in the thickness direction located in a central portion of the support wall portion 72a where the pressure sensor portion 71 is disposed.

The circumferential wall portion 72b is erected up from the outer circumference of the support wall portion 72a on the opposite side to the living body, and the recess portion 72c that opens to the rear surface side of the sensor base 72 is formed by the support wall portion 72a and the circumferential wall portion 72b. Recesses and protrusions are formed along the first direction in the rear surface of the support wall portion 72a. Specifically, ridge portions 72i that extend in the first direction along the longitudinal direction of the pressure sensor portion 71 are formed on the rear surface of the support wall portion 72a in a region in both side portions on either side of the region where the pressure sensor portion 71 is disposed.

The sensor head cover 73 is formed from a synthetic resin, for example, and has a rectangular shape with a central portion projecting to the living body side. The sensor head cover 73 includes, integrally, a protrusion portion 73b including the opening 73a and the frame portion 73c disposed on the circumferential edge of the protrusion portion 73b.

The protrusion portion 73b has a plate-like shape including the rectangular opening 73a. At least the central portion of the main surface that comes into contact with the living body on one side of the protrusion portion 73b is formed flat. The main surface on the other side of the protrusion portion 73b has a tapered shape including an inclined surface 73g that inclines to one side toward the opening 73a centrally located. Moreover, the inner wall of a corner portion 73h, which is the boundary between the protrusion portion 73b and the frame portion 73c, is rounded by surface processing and formed with a curved surface. The sensor head cover 73 has a configuration having no corners, from the inner wall of the frame portion 73c positioned on the outer circumference, along the curved surface of the corner portion 73h, to the opening 73a. A gap portion 79 between the sensor head cover 73 and the sensor base 72 is formed with low fluid resistance.

The frame portion 73c is erected from the circumferential edge of the protrusion portion 73b on the sensor base 72 side and engages with the step portion 72*j* of the outer circumferential edge of the support wall portion 72*a* of the sensor base 72.

At least a portion of the opposing surfaces of the sensor head cover 73 and the sensor base 72 are separated from one another, and the gap portion 79 is formed between the inner surface of the sensor head cover 73 and the outer surface of the sensor base 72. The pressure sensor portion 71 and the soft portion 74 are disposed in the gap portion 79.

In the present embodiment, the gap portion 79 is formed, as a gap, between the surface on one side of the support wall portion 72*a* on which the pressure sensor portion 71 is mounted and the surface on the other side of the protrusion portion 73*b*, and the gap portion 79 is formed between the outer circumferential surface of the support wall portion 72*a* and the inner circumferential surface of the frame portion.

The gap portion 79 communicates with the plurality of flow holes 72*d* to 72*g* of the sensor base 72 through the cutout portion 71*g* of the flexible substrate 71*a* and the opening 71*f* of the adhesive sheet 71*e*. In other words, the gap portion 79 formed a flow path from the plurality of flow holes 72*d* to 72*g* to the opening 73*a*. The soft portion 74 is formed by filling the gap portion 79 with a soft resin material to a position at a predetermined height whereby at least the pressure sensitive elements 71*c* are covered.

The soft portion 74 is formed from a relatively soft resin material such as a silicone resin. The soft portion 74 is provided in the opening 73*a* of the sensor head cover 73 and protects the pressure sensitive elements 71*c* by covering the pressure sensor portion 71. The soft portion 74 is formed, for example, by injecting a soft resin material into the opening 73*a*. An end surface 74*a* of the soft portion 74 is formed flush with the end surface of the sensor head cover 73. Note that it is sufficient that the soft portion 74 comes into contact with the wrist 100 and is formed from a material that allows the pressure of the radial artery 110 to be detected by the pressure sensitive elements 71*c*, and the thickness, shape that comes into contact with the wrist 100, and material of the soft portion 74 can be selected as appropriate.

Next, a method for manufacturing the blood pressure measurement device and the sensor module will be described with reference to FIGS. 13 to 21. The method for manufacturing the blood pressure measurement device and the sensor module includes: a sensor setting step of setting the pressure sensor portion 71 on the sensor base 72 (step ST1), a cover attaching step of attaching the sensor head cover 73 to the sensor base 72 (step ST2), and a filling step of supplying the soft resin with the opening 73*a* closed off by an opposing member (step ST3).

First, in the sensor setting step (step ST1), the pressure sensor portion 71 is set on the sensor base 72 via the adhesive sheet 71*e*. Specifically, first, the plurality of pressure sensitive elements 71*c* are mounted on the substrate 71*b*. Next, the substrate 71*b* on which the plurality of pressure sensitive elements 71*c* are mounted is mounted on the flexible substrate 71*a*. In this way, the pressure sensor portion 71 is completed. Next, the pressure sensor portion 71 is fixed on the sensor base 72 via the adhesive sheet 71*e*.

Then, in the cover attaching step (step ST2), the sensor head cover 73 is put on the sensor base 72. At this time, the pressure sensor portion 71 is disposed in an area corresponding to the opening 73*a* of the sensor head cover 73. Also, the gap portion 79 is formed between the sensor base 72 and the sensor head cover 73. The gap portion 79 forms a flow path from the opening 73*a*, through the opening 71*f* and the cutout portion 71*g* of the flexible substrate 71*a* and the adhesive sheet 71*e* and the flow holes 72*d* to 72*g* of the sensor base 72, to the recess portion 72*c* on the rear side of the sensor base 72.

In the filling step (step ST3), first, with the sensor base 72 and the sensor head cover 73 in an assembled state, the sensor base 72 and the sensor head cover 73 are disposed with the sensor head cover 73 side facing downward, opposite an opposing plate 81 (opposing member) having a smooth surface 81*a*, closing off the opening 73*a*. In this state, a nozzle 82 that discharges a soft resin material is inserted into the first hole 72*d* and the second hole 72*e*, and the soft resin material is supplied via the first hole 72*d* and the second hole 72*e*. For example, due to its own weight, the soft resin material flows from the first hole 72*d* into the gap portion 79 and fills up the gap portion 79 to a position at a predetermined height covering the pressure sensor portion 71. In this manner, the soft resin material is disposed in the opening 73*a*. At this time, the other holes 72*f*, 72*g* are flow outlets for discharging air and excess amounts of the resin material.

Here, the direction of flow is set so that the resin flows from the holes 72*d*, 72*e* serving as flow inlets toward the other holes 72*f*, 72*g*. In the sensing area in which the pressure sensor portion 71 is centrally disposed, a weld line can be prevented from being formed. In other words, when the resin material flows from the holes on both sides toward the center, the resin material flowing in from both sides tends to come together at a central section that affects sensing and form a weld line. If a weld line is formed in the soft portion of the sensing portion (sensitive portion), the transfer of pressure is slightly different. This greatly affects sensing compared to a uniform state with no weld line. In the present embodiment, because the resin material is made to flow from one direction, a weld line can be prevented from being formed at a location that affects sensing. Thus, a negative effect on sensing can be prevented and defects such as weld lines and cracks can be minimized or prevented. In addition, the first hole 72*d* and the second hole 72*e* have a greater opening area than the third hole 72*f* and the fourth hole 72*g*, and the first hole 72*d* has a tapered shape. This allows the filling process to be performed smoothly.

The soft portion 74 is formed by cooling or heating the soft resin material disposed in the gap portion 79 including the opening 73*a*, depending on the type of soft resin material, and solidifying the soft resin material. The sensor base 72, a support plate 77, a circuit board 78, and the sensor head cover 73 are adhered and fixed together by the soft portion 74. After the soft portion 74 is formed, the opposing plate 81 is removed at a predetermined timing. After the soft portion 74 is formed and the opposing plate 81 is removed, the soft portion 74 may be subjected to surface treatment further. In this manner, the sensor module 63 is completed.

With the blood pressure measurement device 1 worn on the wrist 100, the movable base 64 is supported in the movable case 61 in a manner allowing the movable base 64 to move in a direction toward and a direction away from the wrist 100. For example, the movable base 64 is configured to move along the plurality of cylindrical members provided in the movable case 61, for example. The end portion of the movable base 64 on the wrist 100 side is fixed to the sensor base 72. Thus, the movable base 64 supports the sensor base 72 in a manner allowing the sensor base 72 to move in one direction with respect to the movable case 61.

As illustrated in FIG. 22, the adjustment portion 53 is configured to adjust the position of the sensor unit 52, with respect to the case 51, in the circumferential direction of the wrist 100. The adjustment portion 53 is located on the outer surface of the case 51 and includes an adjustment catch 53a, the portion of which is fixed to the fixing portion 61b of the movable case 61 via the third hole portion 51e. Also, the adjustment portion 53 includes: graduations 53b provided adjacent to the third hole portion 51e of the case 51 and an instruction portion 53c provided on the adjustment catch 53a that indicates the graduations 53b.

The adjustment catch 53a is connected to the sensor unit 52 by being fixed to the movable case 61. The adjustment catch 53a is configured to move the sensor unit 52. In other words, the adjustment portion 53 is an adjustment mechanism that, by the adjustment catch 53a being moved in the longitudinal direction of the third hole portion 51e, moves the sensor unit 52 along the second groove 51f2 and adjusts the position of the sensor unit 52 with respect to the case 51.

The graduations 53b and the instruction portion 53c are display portions that display the position of the adjustment catch 53a, i.e., the position of the sensor unit 52 connected to the adjustment catch 53a, in a visually recognizable manner.

The fastener 43 includes, for example, one or a plurality of band-like bands and a fixing member such as a hook-and-loop fastener that secures the band wrapped around the wrist 100. The fastener 43 fixes the attach portion 41 and the sensing body 42 to the wrist 100. Note that the fastener 43 may be composed of: a first belt referred to as a parent that includes a buckle; and a second belt referred to as a pointed end that is fixed to the buckle. Also, the fastener 43 may further have a configuration in which the case 51 is fixed to the attach portion 41 by the fastener 43 being wrapped around the case 51.

In other words, the fastener 43 is configured to prevent the case 51 from moving in a direction away from the attach portion 41 when the reaction force, when the sensor module 63 presses against the wrist 100 due to the expansion of the air bag 62, acts on the movable case 61 and when the case 51 is directly pressed by the movable case 61 or indirectly pressed via the adjustment catch 53a from the movable case 61.

Next, an example of measurement of a blood pressure value using the blood pressure measurement device 1 will be described using FIGS. 23 to 26. FIG. 23 is a flowchart illustrating an example of a blood pressure measurement using the blood pressure measurement device 1, illustrating both the operation of the user and the operation of the control unit 33. FIGS. 24 to 26 are explanatory diagrams illustrating an example of blood pressure measurement using the blood pressure measurement device 1.

First, the user searches by palpating the wrist 100 for the position of the radial artery 110 (step ST11). For example, at this time, a visible line may be drawn on the skin above the radial artery 110 with a pen.

The user then separates the sensing body 42 of the sensor device 5 from the attach portion 41. In the present embodiment, the user operates the engagement portion 51b to release the engagement of the case 51 with the base portion 41a and rotates the sensing body 42 about the rotation shaft 51a in a direction away from the attach portion 41.

The user then attaches the device body 4 and the sensor device 5 as illustrated in FIG. 24 (step ST12). As a specific example, the user first passes the wrist 100 through the body fastener 16 of the device body 4 and the fastener 43 of the sensor device 5 and places the device body 4 and the sensor device 5 at a predetermined position on the wrist 100. Next, the body fastener 16 of the device body 4 is tightened, and the device body 4 is fixed to the wrist 100. Here, in a case of configuration in which a cuff is provided on the body fastener 16 of the device body 4, a check is performed to see whether the skin of the wrist 100 is caught in the body fastener 16 (cuff) and whether the body fastener 16 (cuff) is too loose is performed. Next, the position of the sensor device 5 is adjusted so that the opening portion 41b of the attach portion 41 of the sensor device 5 is located at the radial artery 110 of the wrist 100. In addition, the user tightens the fastener 43 of the sensor device 5, and the sensor device 5 is fixed to the wrist 100, with the radial artery 110 held at the position of the opening portion 41b.

Next, as illustrated in FIG. 25, the user palpates the wrist 100 from the opening portion 41b of the attach portion 41 (step ST13) and checks again that the radial artery 110 is located at the opening portion 41b. Then, as illustrated in FIG. 26, the user rotates the sensing body 42 in a direction toward the attach portion 41 and fixes the sensing body 42 to the attach portion 41 via the engagement portion 51b. Note that when the position of the sensing body 42 is misaligned with the radial artery 110, the adjustment catch 53a is operated to adjust the position of the sensing body 42.

Next, the user operates the operation portion 12 to send an instruction to measure the blood pressure. The control unit 33 measures the blood pressure on the basis of the blood pressure measurement instruction (step ST14). At this time, the control unit 33 drives and controls the pump 14, and, as illustrated in FIGS. 7 to 12, the air bag 62 is expanded, moving the sensor module 63 progressively toward the wrist 100 from a state of being housed inside the movable case 61, and the sensor head cover 73 and the soft portion 74 of the sensor module 63 are pressed against the region where the radial artery 110 of the wrist 100 is found, as illustrated in FIGS. 9 and 12. By pressing the sensor head cover 73 and the soft portion 74 against this region of the wrist 100, the radial artery 110 is pressed with an appropriate amount of pressure so that a portion of the radial artery 110 is flattened, as illustrated in FIG. 12. In this state, the pressure sensitive elements 71c of the pressure sensor portion 71 measure the pressure pulse waves.

Note that the control unit 33 obtains the blood pressure via the tonometry method from the pressure pulse waves of the radial artery 110 detected by the pressure sensor portion 71. Note that prior to blood pressure measurement, the control unit 33 may perform a blood pressure measurement for calibration on the basis of program data stored in the storage unit 32 or may perform a check to determine whether or not the worn state of the device body 4 and/or the sensor device 5 and the position of the pressure sensor portion 71 are correct.

As described above, according to the blood pressure measurement device 1 according to an embodiment of the present invention, the sensor module 63 is provided with the sensor base 72 including the support wall portion 72a that includes the holes 72d to 72g, With this configuration, the soft portion 74 can be formed by filling the soft resin from the rear side of the sensor base 72. Thus, for example, with the opening 73a of the sensor head cover 73 in a state of being disposed opposite the smooth surface 81a, because the soft resin is filled from the other main surface side of sensor base 72, the process of forming the soft portion 74 is made easy. Additionally, the soft resin can be injected from any of the inhomogeneously disposed hole portions, allowing the flow of the soft resin to be set. Thus, the soft portion 74 can be reliably filled on the surface of the pressure sensor portion 71, and a highly smooth surface can be formed. Accordingly, compared to a process in which the soft resin is filled from the opening side of one main surface and a smooth surface is then pressed against the opening, the process can be simplified and a highly smooth surface can be formed. Additionally, the load on the pressure sensor array can be reduced, and high sensor accuracy can be ensured.

In addition, since the shape and disposition of flow holes 72d to 72g can be inhomogeneous, the direction of the flow can be set. In other words, by setting the flow of the soft resin to one direction, the bias of the soft resin material can be prevented, and the formation of a weld line on the sensor 71a that causes a decrease in sensing accuracy or defects can be prevented.

In addition, for example, in the present embodiment, by the flow holes on one side portion side serving as flow inlets and the other flow holes on the other side portion side serving as flow outlets for excess filler and air, the flow direction of the soft resin can be set and the filling step can be promoted.

In addition, the sensor module 63 includes the gap portion 79 including the inclined surface 73g with a tapered shape that is inclined toward the central region where the pressure sensor portion 71 is disposed. This promotes the inflow of the resin material and promotes defoaming near the sensor surface. Because the gap portion 79 has a configuration in which the inner wall has no corners and the resistance is low, the inflow of the resin material can be promoted and the resin can be filled due to its own weight, without using pressure or temperature.

Note that while the assembly time can be shortened by injecting the resin material at the appropriate location and simultaneously performing cooling treatment or heating treatment to harden the soft resin material, in such a case, a weld line is more likely to form. Thus, the configuration of the present embodiment is useful.

Note that the present invention is not limited to the embodiment described above. For example, in the example described above, a configuration has been described in which two of the flow holes 72d, 72e arranged side by side on one side are used as the injection opening in the filling step, but the present invention is not limited thereto. For example, as illustrated in FIG. 27, there may be only one flow inlet, and the soft resin material may be supplied from one of the holes 72d. In this case, the direction of the flow is set to one direction, and a weld line is unlikely to form. Note that another aspect that may be adopted, the soft resin material is injected into three or more of the flow holes using, for example, three or more of the nozzles 82.

In the example described above, the blood pressure measurement device 1 has a configuration in which the device body 4 and the sensor device 5 are different bodies. However, no such limitation is intended. For example, as illustrated in FIGS. 28 and 29, the blood pressure measurement device 1 may have a configuration in which the device body 4 and the sensor device 5 are integrally formed. The blood pressure measurement device 1 with such a configuration, for example, may have configuration in which the operation portion 12, the display portion 13, the pump 14, and the control board 15 used in the device body 4 are provided in the case 51 of the sensing body 42.

Also, in the example described above, the blood pressure measurement device 1 has a configuration in which the sensing body 42 moves in a direction away and a direction toward the attach portion 41 by the sensing body 42 rotating with respect to the attach portion 41 about an axis. However, no such limitation is intended. For example, as illustrated in FIG. 30, the blood pressure measurement device 1 may have a configuration in which the sensing body 42 moves in a direction away and a direction toward the attach portion 41 by the attach portion 41 and the sensing body 42 being separated. In the case in which the blood pressure measurement device 1 has this configuration, the engagement portions 51b are provided at a plurality of positions on the case 51 of the sensing body 42, and the sensing body 42 engages with the attach portion 41 at these positions.

Furthermore, for example, a configuration in which the sensing body 42 rotates with respect to the attach portion 41 about a single axis is also not limited to the example described above. In other words, the example described above has a configuration in which the sensing body 42 rotates with respect to the attach portion 41 about a single axis extending in a direction orthogonal to the circumferential direction of the wrist 100. However, no such limitation is intended. In other words, the sensing body 42 may rotate with respect to the attach portion 41 about a single axis extending in the direction of a tangent line to the circumferential direction of the wrist 100.

Also, in the examples described above, the blood pressure measurement device 1 measures the pressure of the radial artery 110 and obtains the blood pressure by the tonometry method. However, no such limitation is intended. In another example, the pressure of the ulnar artery is measured. The blood pressure measurement device 1 may also have a configuration in which the blood pressure is obtains via a method other than the tonometry method.

In the examples described above, the opening portion 41b of the attach portion 41 has a shape that allows for palpation of the wrist 100. However, no such limitation is intended. That is, for example, the opening portion 41b of the attach portion 41 may have a shape that allows the sensor unit 52 to come into contact with wrist 100 beyond the opening portion 41b, in a range in which position is adjusted by the adjustment portion 53. In addition, similarly, the present invention is not limited to a device for measuring blood pressure and may be applied to other devices using other measurement methods such as devices for measuring pulse waves.

Also, in the example described above, the sensor unit 52 has a configuration in which the sensor base 72 of the sensor module 63 is supported by the movable base 64 in a manner allowing the sensor base 72 to move within the movable case 61. However, no such limitation is intended. For example, the movable base 64 may be integrally formed with the sensor base 72 of the sensor module 63.

In other words, the embodiments described above are merely examples of the present invention in all respects. Of course, various modifications and variations can be made without departing from the scope of the present invention. Thus, specific configurations in accordance with an embodiment may be adopted as appropriate at the time of carrying out the present invention.

REFERENCE SIGNS LIST

1 Blood pressure measurement device
4 Device body
5 Sensor device
11 Body case
12 Operation portion
13 Display portion
14 Pump
14a Tube
15 Control board
15a Cable
16 Body fastener
21 Button
31 Communication unit 32 Storage unit
33 Control unit
41 Attach portion
41a Base portion
41b Opening portion
41c Attachment portion
42 Sensing body
43 Fastener
51 Case
51a Rotation shaft
51b Engagement portion
51c Hole portion
51d Hole portion
51e Hole portion
51f Guide groove
51f1 Groove
51f2 Groove
52 Sensor unit
53 Adjustment portion
53b Graduations
53c Instruction portion
61 Movable case
61a Guide projection
61b Fixing portion
62 Air bag
63 Sensor module
71 Pressure sensor portion
71a Flexible substrate
71b Substrate
71c Pressure sensitive element
71d Pressure sensitive element array
71e Adhesive sheet
71f Opening
71g Cutout portion
72 Sensor base
72a Support wall portion
72b Circumferential wall portion
72c Recess portion
72d to 72h Flow hole (first hole, second hole, third hole, fourth hole, fifth hole)
72i Ridge portion
72j Step portion
73 Sensor head cover
73a Opening
73b Protrusion portion
73c Frame portion
73g Inclined surface
73h Corner portion
74 Soft portion
74a End surface
81 Opposing plate
81a Smooth surface
82 Nozzle
100 Wrist
110 Radial artery
111 Radius
112 Ulnar artery
113 Ulna
114 Tendon

The invention claimed is:

1. A sensor module, comprising:
  a sensor;
  a sensor base including a support wall with a flow hole formed extending through the support wall from one main surface side to an other main surface side, the sensor being disposed on the one main surface side of the sensor base;
  a sensor head cover including an opening at a position opposite the sensor and disposed on the one main surface side of the support wall of the sensor base with a gap that communicates with the flow hole and the opening formed therebetween; and
  a soft material disposed in the opening that covers the sensor, wherein
  the flow hole is an inflow hole through which a resin material that forms the soft material flows in the opening on the one main surface side from the other main surface side.

2. The sensor module according to claim 1, wherein
  a plurality of the flow holes are disposed asymmetrically with respect to the sensor in an outer circumference of a region where the sensor is disposed.

3. The sensor module according to claim 2, wherein
  the sensor includes a pressure sensitive element array including one or more pressure sensitive elements;
  one or the plurality of flow holes are formed in both side portions on either side of the pressure sensitive element array that extends in a predetermined first direction; and
  a sum of opening areas of the flow holes on one side is greater than a sum of opening areas of the flow holes on an other side.

4. The sensor module according to claim 3, wherein
  a surface of the sensor head cover opposite the sensor base includes an inclined surface inclined toward the opening.

5. A blood pressure measurement device, comprising:
  the sensor module according to claim 3;
  a sensing body including a case that houses the sensor module;
  an attach mechanism including: an opening portion disposed at a position opposite a region where one artery of a wrist is present, the opening portion having a shape that allows the wrist to be palpated, and an end surface that curves conforming to a portion of a shape in a circumferential direction of the wrist; and
  a fastener provided on the attach mechanism.

6. The sensor module according to claim 2, wherein
  a surface of the sensor head cover opposite the sensor base includes an inclined surface inclined toward the opening.

7. A blood pressure measurement device, comprising:
  the sensor module according to claim 2;
  a sensing body including a case that houses the sensor module;
  an attach mechanism including: an opening portion disposed at a position opposite a region where one artery of a wrist is present, the opening portion having a shape that allows the wrist to be palpated, and an end surface that curves conforming to a portion of a shape in a circumferential direction of the wrist; and
  a fastener provided on the attach mechanism.

8. The sensor module according to claim 2, wherein
  at least one of the flow holes has a different opening area to another of the flow holes.

9. The sensor module according to claim 8, wherein
  the sensor includes a pressure sensitive element array including one or more pressure sensitive elements;
  one or the plurality of flow holes are formed in both side portions on either side of the pressure sensitive element array that extends in a predetermined first direction; and a sum of opening areas of the flow holes on one side is greater than a sum of opening areas of the flow holes on an other side.

10. The sensor module according to claim 9, wherein a surface of the sensor head cover opposite the sensor base includes an inclined surface inclined toward the opening.

11. A blood pressure measurement device, comprising:
the sensor module according to claim 9;
a sensing body including a case that houses the sensor module;
an attach mechanism including: an opening portion disposed at a position opposite a region where one artery of a wrist is present, the opening portion having a shape that allows the wrist to be palpated, and an end surface that curves conforming to a portion of a shape in a circumferential direction of the wrist; and
a fastener provided on the attach mechanism.

12. The sensor module according to claim 8, wherein a surface of the sensor head cover opposite the sensor base includes an inclined surface inclined toward the opening.

13. A blood pressure measurement device, comprising:
the sensor module according to claim 8;
a sensing body including a case that houses the sensor module;
an attach mechanism including: an opening portion disposed at a position opposite a region where one artery of a wrist is present, the opening portion having a shape that allows the wrist to be palpated, and an end surface that curves conforming to a portion of a shape in a circumferential direction of the wrist; and
a fastener provided on the attach mechanism.

14. The sensor module according to claim 1, wherein the sensor includes a pressure sensitive element array including one or more pressure sensitive elements;
one or a plurality of the flow holes are formed in both side portions on either side of the pressure sensitive element array that extends in a predetermined first direction; and
a sum of opening areas of the flow holes on one side is greater than a sum of opening areas of the flow holes on an other side.

15. The sensor module according to claim 14, wherein a surface of the sensor head cover opposite the sensor base includes an inclined surface inclined toward the opening.

16. A blood pressure measurement device, comprising:
the sensor module according to claim 14;
a sensing body including a case that houses the sensor module;
an attach mechanism including: an opening portion disposed at a position opposite a region where one artery of a wrist is present, the opening portion having a shape that allows the wrist to be palpated, and an end surface that curves conforming to a portion of a shape in a circumferential direction of the wrist; and
a fastener provided on the attach mechanism.

17. The sensor module according to claim 1, wherein a surface of the sensor head cover opposite the sensor base includes an inclined surface inclined toward the opening.

18. A blood pressure measurement device, comprising:
the sensor module according to claim 17;
a sensing body including a case that houses the sensor module;
an attach mechanism including: an opening portion disposed at a position opposite a region where one artery of a wrist is present, the opening portion having a shape that allows the wrist to be palpated, and an end surface that curves conforming to a portion of a shape in a circumferential direction of the wrist; and
a fastener provided on the attach mechanism.

19. A blood pressure measurement device, comprising:
the sensor module according to claim 1;
a sensing body including a case that houses the sensor module;
an attach mechanism including: an opening portion disposed at a position opposite a region where one artery of a wrist is present, the opening portion having a shape that allows the wrist to be palpated, and an end surface that curves conforming to a portion of a shape in a circumferential direction of the wrist; and
a fastener provided on the attach mechanism.

20. A method for manufacturing a sensor module, comprising:
disposing
a sensor base including a support wall with a flow hole formed extending through the support wall from one main surface side to an other main surface side, a sensor being disposed on the one main surface side of the sensor base and
a sensor head cover including an opening at a position opposite the sensor
opposite one another, with the one main surface side facing downward and with a gap that communicates with the flow hole and the opening formed between the sensor head cover and the one main surface of the sensor base; and
supplying a resin material from the other main surface side of at least any one of the flow holes, with an opposing member including a flat surface brought into contact under the sensor head cover, the flat surface of the opposing member closing off the opening.

* * * * *